US006455499B1

(12) United States Patent
Roeske

(10) Patent No.: US 6,455,499 B1
(45) Date of Patent: *Sep. 24, 2002

(54) METHODS FOR TREATING DISORDERS ASSOCIATED WITH LHRH ACTIVITY

(75) Inventor: Roger W. Roeske, Indianapolis, IN (US)

(73) Assignee: Indiana University Foundation, Bloomington, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/256,599

(22) Filed: Feb. 23, 1999

Related U.S. Application Data

(62) Division of application No. 08/973,378, filed as application No. PCT/US96/09852 on Jun. 7, 1996.

(51) Int. Cl.[7] ............................................. A61K 38/08
(52) U.S. Cl. ............................ 514/15; 514/2; 930/130
(58) Field of Search .................................. 514/2, 15

(56) References Cited

U.S. PATENT DOCUMENTS

| | | | |
|---|---|---|---|
| 3,787,385 A | 1/1974 | Folkers et al. | 260/112.5 |
| 3,953,416 A | 4/1976 | Folkers et al. | 260/112.5 |
| 3,974,135 A | 8/1976 | Folkers et al. | 260/112.5 |
| 4,215,038 A | 7/1980 | Rivier et al. | 260/112.5 |
| 4,244,946 A | 1/1981 | Rivier et al. | 424/177 |
| 4,292,313 A | 9/1981 | Vale, Jr. et al. | 424/177 |
| 4,307,083 A | 12/1981 | Rivier et al. | 424/177 |
| 4,377,574 A | 3/1983 | Rivier et al. | 424/177 |
| 4,386,074 A | 5/1983 | Vale, Jr. et al. | 424/177 |
| 4,444,759 A | 4/1984 | Rivier et al. | 424/177 |
| 4,489,061 A | 12/1984 | Rivier et al. | 424/177 |
| 4,504,414 A | 3/1985 | Folkers et al. | 260/112.5 |
| 4,547,370 A | 10/1985 | Roeske | 514/15 |
| 4,565,804 A | 1/1986 | Rivier et al. | 514/15 |
| 4,569,927 A | 2/1986 | Rivier et al. | 514/15 |
| 4,619,914 A | 10/1986 | Vale, Jr. et al. | 514/15 |
| 4,642,332 A | 2/1987 | Folkers et al. | 260/112.5 |
| 4,647,653 A | 3/1987 | Coy | 530/313 |
| 4,656,247 A | 4/1987 | Folkers et al. | 260/112.5 |
| 4,661,472 A | 4/1987 | Rivier et al. | 514/15 |
| 4,677,193 A | 6/1987 | Rivier et al. | 530/313 |
| 4,689,396 A | 8/1987 | Roeske et al. | 530/313 |
| 4,721,775 A | 1/1988 | Folkers et al. | 530/313 |
| 4,740,500 A | 4/1988 | Vale, Jr. et al. | 514/15 |
| 4,801,577 A | 1/1989 | Nestor, Jr. et al. | 514/15 |
| 4,851,385 A | 7/1989 | Roeske | 514/15 |
| 4,866,160 A | 9/1989 | Coy et al. | 530/313 |
| 4,935,491 A | 6/1990 | Folkers et al. | 530/313 |
| 4,992,421 A | 2/1991 | De et al. | 514/19 |
| 5,003,011 A | 3/1991 | Coy et al. | 530/328 |
| 5,064,939 A | 11/1991 | Rivier et al. | 530/317 |
| 5,073,624 A | 12/1991 | Coy et al. | 530/313 |
| 5,110,904 A | 5/1992 | Haviv et al. | 530/313 |
| 5,140,009 A | 8/1992 | Haviv et al. | 514/16 |
| 5,169,932 A | 12/1992 | Hoeger et al. | 530/313 |
| 5,171,835 A | 12/1992 | Janaky et al. | 530/313 |
| 5,180,711 A | 1/1993 | Hodgen | 514/15 |
| 5,296,468 A | 3/1994 | Hoeger et al. | 514/15 |
| 5,300,492 A | 4/1994 | Haviv et al. | 514/15 |
| 5,352,796 A | 10/1994 | Hoeger et al. | 548/265.2 |
| 5,371,070 A | 12/1994 | Koerber et al. | 514/9 |
| 5,413,990 A | 5/1995 | Haviv et al. | 514/15 |
| 5,470,947 A | 11/1995 | Folkers et al. | 530/313 |
| 5,843,901 A | * 12/1998 | Roeske | 514/15 |

FOREIGN PATENT DOCUMENTS

| | | |
|---|---|---|
| EP | 0 328 090 | 8/1989 |
| FR | 2 329 294 | 5/1977 |
| WO | WO89/01944 | 3/1989 |
| WO | WO92/20711 | 11/1992 |
| WO | WO95/04540 | 2/1995 |

OTHER PUBLICATIONS

Coy, D.H. et al., (1976), "Analogs of Luteinizing Hormone–Releasing Hormone with Increased Biological Activity Produced by D–Amino Acid Substitution at Position 6", *J. Med. Chem.*, 19, pp. 423–425.

Du, Y–C. "Peptides: Biology, Chemistry; Proc. 1992 Chinese Pept. Symp." (1993), Tian, Z. et al. "Structure–activity Studies of LHRH Antagonists with Sidechain Modified D–Lys(6)" pp. 45–48.

Flouret, G., et al. "Antiovulatory Antagonists of LHRH Related To Antide", *Journal of Peptide Science*, vol. 1, pp. 89–105, (1995).

Folkers, K. et al. (1986), "Increased Potency of Antagonists of the Luteinizing Hormone Releasing Hormone Which Have D–3–Pal in Position 6", *Biochem. Biophys. Res. Comm.* 137(2):709–715.

Furr, B.J.A. et al., (1988), "Luteinizing Hormone–Releasing Hormone and its Analogues: A Review of Biological Properties and Clinical Uses", *J. Endocrinol. Invest.*, 11, pp. 535–557.

Janecka, A., et al., (1994), "New Highly Active Antagonists of LHRH with Acylated Lysine and p–Aminophenylalanine in Positions 5 and 6", Int. J. Peptide Protein Res., 44, pp. 19–23.

Karten, M.J. et al, (1986), Synthesis and Biological Activity of Some Very Hydrophobic Superagonist Analogues of Luteinizing Hormone.

Ljungqvist, A. et al. "Antide and Related Antagonists of Luteinizing Hormone Release with Long Action and Oral Activity" Proceedings of the *National Academy of Sciences of the USA* 85(21):8236–8240 (1998).

Nestor, J.J. et al., (1982); "Synthesis and Biological Activity of Some Very Hydrophobic Superagonist Analogues of Luteinizing Hormone–Releasing Hormone", *J. Med. Chem.*, 25, pp. 795–801.

(List continued on next page.)

*Primary Examiner*—Michael Borin
(74) *Attorney, Agent, or Firm*—Lahive & Cockfield LLP; Giulio A. DiConti; Maria C. Laccotripe

(57) ABSTRACT

Methods of treating a subject having a disorder associated with LHRH activity are disclosed.

23 Claims, 3 Drawing Sheets

OTHER PUBLICATIONS

Nestor, J.J., (1987), "Design of LHRH Agonist Drug Candidates", *J. Andrology.*, 8, pp. S4–S8.

River, J. et al., "Gonadotropin–Releasing Hormone Antagonists with $N^W$Triazolylornithine, –lysine, or –p–aminophenylalnine Residues at Positions 5 and 6" *Journal of Medicinal Chemistry 35(23)*: 4270–4278 (1992).

Sandow, E.A., et al. "Studies on Enzyme Stability of Luteinizing Hormone Releasing Hormone Analogs" *Chemical Abstracts*, vol. 91, Abstract No. 91:187020a, pp. 87–88, (1979).

Tian, Z.P. et al., (1994), "Design and Synthesis of Highly Water Soluble LHRH Antagonists", Pept.: Chem., Struct. Biol., Proc. Am. Pept. Symp., 13th, 562–564.

Tian, Z.P. et al., (1993), "Structure–activity Studies of LH–RH Antagonists with Side–Chain Modified D–lysine in Position 6", Pept.: Biol. Chem., Proc. Chin. Pept. Symp., 45–48.

Zhang, Y. et al., (1993), "N–Alkylation of Pyridylalanine and Pryidinecarboxylic Acids and Their Use in Synthesis of GnRH Antagonists", *Tetrahedron Letters*, 34(23): 3659–3662.

Zhang, Y.L. et al., (1994), "Structure–activity Relationships of LHRH Antagonists: Incorporation of Positively Charged $N^{py}$–alkylated 3–D–pyridylalanines", Pept.: Chem. Struct. Biol. Proc. Am Pept. Symp., 13th, 565–567.

* cited by examiner

METHODS FOR TREATING DISORDERS ASSOCIATED WITH LHRH ACTIVITY

This application is a divisional application of Ser. No. 08/973,378 filed on Apr. 6, 1998, pending, which is a national application under 35 U.S.C. §371(e) corresponding to PCT/US96/09852 filed Jun. 7, 1996, which in turn claims priority to U.S. Pat. No. 5,843,901, issued on Dec. 1, 1998. The contents of all of the aforementioned application(s) are incorporated herein by reference.

BACKGROUND OF THE INVENTION

The present invention relates to LHRH antagonist peptides and uses thereof.

Luteinizing hormone (LH) and follicle-stimulating hormone (FSH) are hormones released by the pituitary gland. These hormones regulate the functioning of the gonads and the production and maturation of gametes. LH and FSH are generally released by the pituitary gland upon prior release of triggering hormone from the hypothalamus. Luteinizing hormone-releasing hormone (LHRH; also known as gonadotropin-releasing hormone or GnRH) is one of the principal hypothalamic hormones which triggers the release of LH. Thus, release of LHRH represents a control point in the physiological regulation of gonadal function. The structure of mammalian LHRH has been determined, and has been found to be a decapeptide:

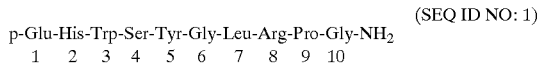
(SEQ ID NO: 1)
p-Glu-His-Trp-Ser-Tyr-Gly-Leu-Arg-Pro-Gly-NH₂
 1    2   3   4   5   6   7   8   9  10

LH release is necessary for ovulation; thus, compounds which inhibit LH release by blocking the action of LHRH are useful as contraceptive agents. LHRH antagonists are also useful for regulating secretion of gonadotropins in male mammals, and thus can be used as male contraceptives. In addition, LHRH antagonists can be used in the treatment of sex-hormone dependent cancers (for example, prostate cancer), where increased levels of gonadotropins increase the rate of tumor growth.

Many modified LHRH analog peptides have been synthesized in an attempt to increase the potency of the antagonists, preferably while also increasing the resistance of the antagonist to enzymatic degradation. For example, synthetic LHRH antagonist peptides which incorporate modified or unnatural amino acids have been tested. Common substitutions include, for example, substitution of 4-Cl-D-Phe for His at position 2, or substitution of D-Ala-NH₂ for Gly-NH₂ at position 10.

One problem frequently encountered in LHRH antagonist peptides is the occurrence of histamine-releasing activity. This histamine-releasing activity represents a serious obstacle to the clinical use of such antagonists because histamine release results in adverse side effects such as edema and itching. Thus, LHRH antagonist peptides which have low histamine releasing activity are particularly desirable. Although the LHRH antagonist and histamine-releasing properties are not necessarily related, very few prior art compounds combine low histamine-releasing activity with high LHRH antagonist activity. Many prior art LHRH antagonist peptides also suffer from poor water-solubility, which complicates formulation of the antagonist for administration.

SUMMARY OF THE INVENTION

The present invention features LHRH antagonist peptides, methods of modulating LHRH activity, and methods of treating a subject with the antagonists of the invention. In one embodiment, an LHRH antagonist comprises a peptide compound, wherein a residue of the peptide compound corresponding to the amino acid at position 6 of natural mammalian LHRH comprises D-Lys(Imdac), D-Lys(Ppic), D-Lys(Dodac), D-Lys(pGlu), D-Lys(Otac) and D-Lys(Onic) or a moiety selected from the group consisting of a dipolar moiety, a sulfonium moiety, a receptor-modifying moiety and a small polar moiety, such that the peptide compound has LHRH antagonist activity, with the provisos that the dipolar moiety is not a zwitterionic pyridinium and the residue is not D-Cit, D-Hci or a lower alkyl derivative of D-Cit or D-Hci. Preferably, the peptide compound comprises about 8 to about 12 residues. More preferably, the peptide compound comprises 10 residues.

In another embodiment, the invention provides a peptide compound comprising a structure:

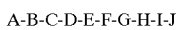

wherein
A is pyro-Glu, Ac-D-Nal, Ac-D-Qal, Ac-Sar, or Ac-D-Pal;
B is His or 4-Cl-D-Phe;
C is Trp, D-Pal, D-Nal, L-Nal, D-Pal(N—O), or D-Trp;
D is Ser;
E is N-Me-Ala, Tyr, N-Me-Tyr, Ser, Lys(iPr), 4-Cl-Phe, His, Asn, Met, Ala, Arg or Ile;
F is D-Lys(Imdac), D-Lys(Ppic), D-Lys(Dodac), D-Lys(pGlu), D-Lys(Otac), D-Lys(Onic) or a structure:

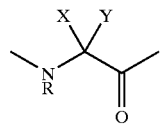

wherein
R and X are, independently, H or alkyl; and
Y comprises a moiety selected from the group consisting a dipolar moiety, a sulfonium moiety, a receptor-modifying moiety and a small polar moiety, the provisos that the dipolar moiety is not a zwitterionic pyridinium and F is not D-Cit, D-Hci or a lower alkyl derivative of D-Cit or D-Hci;
G is Leu or Trp;
H is Lys(iPr), Gln, Met, or Arg;
I is Pro; and
J is Gly-NH₂ or D-Ala-NH₂;
or a pharmaceutically acceptable salt thereof.

The invention also provides pharmaceutical compositions of the LHRH antagonist peptides.

In another aspect, the invention provides a method of inhibiting LHRH activity in a subject, comprising administering to a subject an effective amount of an LHRH antagonist, such that LHRH activity is inhibited.

In another aspect, the invention provides a method of inhibiting LHRH activity in a cell, comprising contacting a cell with an LHRH antagonist, such that LHRH activity is inhibited.

In another aspect, the invention provides a method of inhibiting growth of a hormone-dependent tumor in a subject, comprising administering to a subject an effective amount of an LHRH antagonist, such that tumor growth is inhibited.

In another aspect, the invention provides a method of inhibiting ovulation in a subject, comprising administering to a subject an effective amount of an LHRH antagonist, such that ovulation is inhibited.

In another aspect, the invention provides a packaged formulation for treating a subject for a disorder associated with LHRH activity, comprising an LHRH antagonist packaged with instructions for using the LHRH antagonist for treating a subject having a disorder associated with LHRH activity.

DETAILED DESCRIPTION OF THE INVENTION

Figure 1:
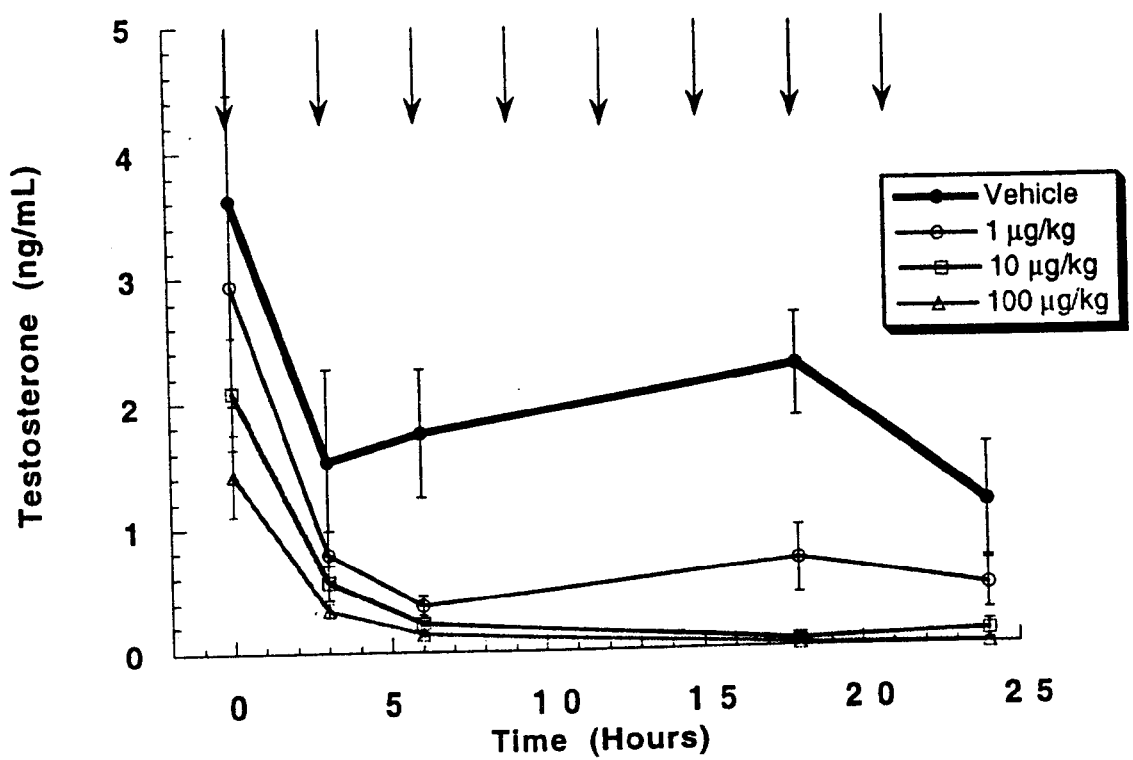
FIG. 1 is a graph depicting plasma testosterone levels (in ng/ml) in adult male rats administered eight subcutaneous injections of the LHRH antagonist #3827, one injection every three hours, at doses of 1, 10 or 100 µg/kg.

In order that the present invention may be more readily understood, certain terms are first defined.

As used herein, "LHRH antagonist peptide" is intended to include peptides and peptide analogs which inhibit LHRH activity (i.e., has "LHRH antagonist activity") in vivo or in vitro. Candidate LHRH antagonist peptides can be assayed, for example, in the animal model described in Corbin and Beattie, *Endocrine Res. Commun.* 2:1 (1975) (and see infra). In this assay, the LHRH antagonistic activity of a candidate compound is assayed by measuring the antiovulatory activity (AOA) of the compound in rats.

The term "histamine-releasing activity", as used herein, refers to the tendency of a compound to release histamine when administered to a subject. The histamine-releasing activity of a compound can be measured with an in vitro assay (described in more detail, infra). Preferred LHRH antagonist peptides have high activity in the rat antiovulatory activity assay, but low histamine releasing activity. Preferred LHRH antagonist peptides have an $ED_{50}$ in the histamine release assay of at least 3 µg/ml, more preferably at least 5 µg/ml, and still more preferably at least 10 µg/ml.

The term "alkyl", as used herein, refers to a straight or branched chain hydrocarbon group having from about 1 to about 10 carbon atoms. The term "lower alkyl" refers to an alkyl group having from about 1 to about 6 carbon atoms. Exemplary lower alkyl groups include methyl, ethyl, n-propyl, isopropyl, n-butyl, isobutyl, sec-butyl, tert-butyl, n-pentyl, and n-hexyl. An alkyl group may be unsubstituted, or may be substituted at one or more positions, with, e.g., halogens, alkyls, cycloalkyls, alkenyls, alkynyls, aryls, heterocycles, hydroxyls, aminos, nitros, thiols, amines, imines, amides, phosphonates, phosphines, carbonyls, carboxyls, silyls, ethers, thioethers, sulfonyls, selenoethers, ketones, aldehydes, esters, —$CF_3$, —CN, or the like. Preferred alkyls are lower alkyls.

The term "cycloalkyl" refers to a cyclic saturated hydrocarbon group having from 3 to 8 carbon atoms. Exemplary cycloalkyls include cyclopropyl, cyclobutyl, cyclopentyl, cyclohexyl, and cyclooctyl. Cycloalkyl groups may be unsubstituted or substituted at one or more ring positions as described for alkyls. Thus, a cycloalkyl may be substituted with, e.g., halogens, alkyls, cycloalkyls, alkenyls, alkynyls, aryls, heterocycles, hydroxyls, aminos, nitros, thiols amines, imines, amides, phosphonates, phosphines, carbonyls, carboxyls, silyls, ethers, thioethers, sulfonyls, selenoethers, ketones, aldehydes, esters, —$CF_3$, —CN, or the like.

The terms "alkenyl" and "alkynyl", as used herein, refer to unsaturated groups analogous in length and possible substitution to the alkyls described above, but which contain at least one carbon-carbon double or triple bond respectively.

The term "aryl" as used herein includes 4-, 5-, 6- and 7-membered single-ring aromatic groups which may include from zero to four heteroatoms, for example, benzene, pyrrole, furan, thiophene, imidazole, oxazole, thiazole, triazole, tetrazole, pyrazole, pyridine, pyrazine, pyridazine and pyrimidine, and the like. Those aryl groups having heteroatoms in the ring structure may also be referred to as "aryl heterocycle" or "heteroaromatic". The aromatic ring can be substituted at one or more ring positions with such substituents as described above, as for example, halogens, alkyls, cycloalkyls, alkenyls, alkynyls, heterocycles, hydroxyls, aminos, nitros, thiols, amines, imines, amides, phosphonates, phosphines, carbonyls, carboxyls, silyls, ethers, thioethers, sulfonyls, selenoethers, ketones, aldehydes, esters, —$CF_3$, —CN, or the like. An aromatic ring may also be substituted with another aromatic ring, as in, for example, a biphenyl. Aryl groups also include fused or polycyclic aromatic systems.

The terms "heterocycle" or "heterocyclic group" refer to 4- to 10-membered ring structures, more preferably 5 to 7 membered rings, which ring structures include one to four heteroatoms. Heterocyclic groups include pyrrolidine, oxolane, thiolane, imidazole, oxazole, piperidine, piperazine, morpholine. The heterocyclic ring can be substituted at one or more positions with such substituents as described above, as for example, halogens, alkyls, cycloalkyls, alkenyls, alkynyls, aryls, other heterocycles, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, —$CF_3$, —CN, or the like. Heterocycles may also be bridged or fused to other cyclic groups as described below.

The terms "polycycle" or "polycyclic group" refer to two or more cyclic rings (e.g., cycloalkyls, cycloalkenyls, cycloalkynyls, aryls and/or heterocycles) in which two or more carbons are common to two adjoining rings, e.g., the rings are "fused rings". Rings that are joined through nonadjacent atoms are termed "bridged" rings. Each of the rings of the polycycle can be substituted with such substituents as described above, as for example, halogens, alkyls, cycloalkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, —$CF_3$, —CN, or the like.

The term "heteroatom" as used herein means an atom of any element other than carbon or hydrogen. Preferred heteroatoms are nitrogen, oxygen, sulfur, phosphorus and selenium.

The term "arylalkyl", as used herein, refers to an aryl group appended to an alkyl group, including, but not limited to, benzyl, naphthylmethyl, pyridyl methyl, and the like.

The term "ylid" is known in the art and refers to a moiety in which a positively charged atom (especially from Groups V and VI of the periodic table) is bonded to a carbon atom which bears an unshared pair of electrons. Thus, an ylid has the resonance forms:

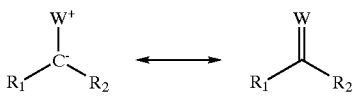

in which W is a heteroatom such as S, or P, and $R_1$ and $R_2$ are, independently, H, alkyl, cycloalkyls, alkenyl, alkynyl, aryl, alkoxy, thioalkoxy, and the like. The heteroatom is substituted with an appropriate number of substituents (i.e., two for N and S, and three for P); the substituents are independently alkyl, cycloalkyl, aryl, and the like. Nitrogen ylides do not have a significant contribution from the non-charge-separated resonance form (on the right, above).

The term "dipolar moiety", as used herein, refers to a covalently bonded moiety having both positive and negative charges (e.g., a zwitterionic moiety). Exemplary dipolar groups include ylids (e.g., of S, N, or P), tertiary amine oxides, nitrones, pyridine-N-oxides, nitrile oxides, quaternary amino acids (e.g., 2-(N,N,N-trialkylammonium) acetate), amino acids, sulfonium arene oxides (as described in, for example, U.S. Pat. No. 4,111,914), betaines (e.g., trigonellin), and the like. In certain preferred embodiments, the dipolar moiety is a pyridine-N-oxide. In other preferred embodiments, the dipolar moiety is a zwitterionic pyridinium moiety. In certain other embodiments, the dipolar moiety is not a zwitterionic pyridinium moiety.

As used herein, a "cationic moiety" is a moiety in which at least one atom bears a positive charge, and the moiety has a net positive charge. Thus, for example, an N-alkyl (or N-alkenyl, -alkynyl, or -aryl, collectively referred to herein as "N-substituted pyridinium") pyridinium moiety can be a cationic moiety (and is referred to herein as a "cationic pyridinium moiety"), but a pyridine-N-oxide is not, unless it has a net positive charge. As described above, a pyridine-N-oxide can be a dipolar moiety. Other exemplary cationic moieties include quaternary amines, sulfonium salts, phosphonium salts, and the like. In certain preferred embodiments, the cationic moiety is a sulfonium moiety.

A sulfonium moiety has the following structure:

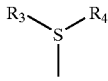

in which $R_3$ and $R_4$ are each, independently, alkyl, cycloalkyl, alkenyl, alkynyl, aryl, and the like.

In other preferred embodiments, the cationic moiety is a cationic pyridinium moiety. A cationic pyridinium moiety has the following structure:

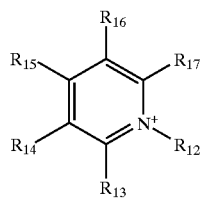

wherein $R_{12}$ is alkyl or aryl, and $R_{13}$–$R_{17}$ are each, independently, hydrogen, halogens, alkyls, cycloalkyls, alkenyls, alkynyls, aryls, other heterocycles, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, —CF$_3$, —CN, or the like. Preferred cationic pyridinium moieties include Pal(iPr) and Pal(Bzl). N-methyl pyridinium moieties are not preferred.

Although the above examples describe pyridine (or pyridinium) moieties, it will be apparent to the skilled artisan that other N-heteroaromatic moieties (that is, a moiety in which at least one nitrogen is present in an aromatic ring) may be substituted for the pyridine (or pyridinium) moieties described herein. Exemplary N-heteroaromatics include thiazole, triazole, tetrazole, pyrazole, pyrazine, pyridazine and pyrimidine, and the like. Thus, N-substituted pyrazines, pyridazines, and the like, are contemplated for use in the present invention.

As used herein, "tertiary amine" includes trialkyl amines, triaryl amines, and amines which have both alkyl and aryl substituents.

As used herein, "zwitterionic pyridinium moiety" refers to a moiety having the form:

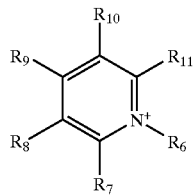

which $R_6$ comprises an alkyl, cycloalkyl, alkenyl, alkynyl, or aryl moiety, and $R_7$–$R_{11}$ are each, independently, hydrogen, halogens, alkyls, cycloalkyls, alkenyls, alkynyls, aryls, other heterocycles, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, —CF$_3$, —CN, or the like, with the proviso that at least one of $R_6$–$R_{11}$ is substituted with an anionic moiety. An "anionic moiety", as used herein, is a moiety which has a net negative charge. The anionic moiety is chosen to be compatible with other moieties, and to form a stable compound. Illustrative anionic moieties include carboxylates, phosphates, phosphonates, sulfates, sulfonates, and the like. In certain preferred embodiments, the anionic moiety is a carboxylate. In other preferred embodiments, the anionic moiety is a sulfonate. In a preferred embodiment, $R_6$ comprises:

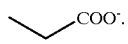

A pyridine N-oxide is a moiety which has the form:

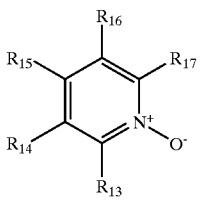

where $R_{13}$–$R_{17}$ have the meanings defined above.

The term "hydrophilic N-acyl moiety", as used herein, refers to a moiety which comprises a nitrogen atom acylated so as to form a hydrophilic moiety. Thus, a hydrophilic N-acyl moiety can have the form:

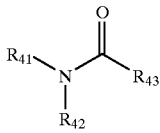

where $R_{41}$ and $R_{42}$, are each, independently, H, alkyl, cycloalkyl, aryl and the like; and $R_{43}$ is alkyl, cycloalkyl, alkenyl, alkynyl, aryl, and the like; and $R_{41}$–$R_{43}$ are selected to form a hydrophilic moiety. In preferred embodiments, $R_{41}$ and $R_{42}$ are not both H.

Relative hydrophilicity can be determined by any of several methods known in the art (Hansch, ed., "Comprehensive Medicinal Chemistry", Vol. 4, Pergamon Press, Oxford, 1990), and can be used to guide the choice of potential hydrophilic moieties for use in the invention. The partition coefficient, P, between 1-octanol and water has been used as a reference for measuring the hydrophilicity of a compound. Hydrophilicity can be expressed as log P, the logarithm of the partition coefficient (Hansch et al., *Nature* 194:178 (1962); Fujita et al., *J. Am. Chem. Soc.* 86:5175 (1964)). Standard tables of hydrophilicity for many molecules, and lipophilicity (hydrophobicity) substituent constants (denoted π) for many functional groups, have been compiled (see, e.g., Hansch and Leo, "Substituent Constants for Correlation Analysis in Chemistry and Biology," Wiley, New York, N.Y., (1979)). The hydrophilicity of a vast range of candidate hydrophilicity moieties can be quite accurately predicted with the aid of these tables. For example, the measured log P (octanol/water) of naphthalene is 3.45. The substituent constant p for —OH is −0.67. Therefore, the predicted log P for β-naphthol is 3.45+(−0.67)=2.78. This value is in good agreement with the measured log P for β-naphthol, which is 2.84. In certain preferred embodiments, the hydrophilic N-acyl moiety has a value of log P between −1 and +2, more preferably between −0.5 and +1.5. Examples of residues incorporating preferred hydrophilic acyl moieties are D-Lys(Imdac), D-Lys(Ppic), D-Lys (Dodac), D-Lys(pGlu), D-Lys(Otac), and D-Lys(Onic). Other preferred residues incorporating hydrophilic acyl moieties include Lys(Imdac), Lys(Ppic), Lys(Dodac), Lys (pGlu), Lys(Otac), and Lys(Onic).

The term "small polar moiety" refers to a moiety which has small steric bulk and is relatively polar. In certain embodiments, a small polar moiety is not D-Cit, D-Hci or lower alkyl derivatives thereof. Polarity is measured as hydrophilicity by the P scale described above. In certain preferred embodiments, the small polar moieties have a log P between −1 and +2. In particularly preferred embodiments, the small polar moiety modifies residue 6. In preferred embodiments, the steric bulk of the small polar moiety is less than the steric bulk of Trp. Examples of residues incorporating preferred small polar moieties are D- or L-Asn, D- or L-Gln, and D- or L-Thr. In preferred embodiments, the small polar moiety is not Glu or a carboxylic ester of Glu. In an especially preferred embodiment, the small polar moiety is D-Asn.

The term "leaving group" is known in the art and, as used herein, refers to a functionality which upon heterolytic bond cleavage departs with an electron pair. In general, good leaving groups are those moieties which are expelled from the substrate as weak bases, whether charged or uncharged. For example, sulfates, sulfonates, sulfides, chloride, bromide, iodide, phosphates, phosphinates, and the like are good leaving groups. In other words, when, for example, a C-S bond of a sulfonium moiety is cleaved, a sulfide departs (with an electron pair).

The term "receptor-modifying moiety", as used herein, refers to a moiety which can modify, covalently or non-covalently, a receptor for an LHRH antagonist peptide. For example, it has recently been shown (C. A. Flanagan et al., (1 994) *J. Biol. Chem.* 269:22636) that Glu301 of the mouse LHRH receptor (which corresponds to Asp301 in the human LHRH receptor) interacts with $Arg^8$ in LHRH agonists. Thus, a carboxylate-modifying reagent (such as an alkylating agent) can modify Glu301 (Asp301) and thus modify the mouse (or human) LHRH receptor. A receptor-modifying moiety may act to bond the LHRH antagonist peptide to the receptor (e.g., esterifying the antagonist to the receptor by displacement of a leaving group), or it may modify the receptor without bonding the LRHR antagonist peptide to the receptor (e.g., by methylation with a methylsulfonium moiety). Other residues of an LHRH receptor can also be modified, and moieties which can modify such residues are also receptor-modifying moieties. Exemplary receptor-modifying reagents include alkyl and benzyl halides (e.g., methyl iodide or benzyl bromide), α-haloketones, α-haloesters and α-haloamides (collectively referred to as "α-halocarbonyls"), sulfonium salts, sulfates, alkyl or aryl sulfonates, and other reagents which comprise a good leaving group as described above. Other receptor-modifying reagents are described in, for example, A. J. Barrett and G. Salvesen, eds. (1986) "Proteinase Inhibitors", *Research Monographs in Cell and Tissue Physiology*, Vol. 12, Elsevier Press, Amsterdam.

Although in certain embodiments an LHRH antagonist of the invention contains a receptor-modifying moiety, the invention is not intended to be limited to those antagonists that actually modify a receptor residue. An LHRH antagonist comprising a receptor-modifying moiety but which does not actually modify the receptor may nonetheless be an effective LHRH antagonist. However, for those antagonists that do modify a receptor residue, one advantage is that such moieties can be designed to selectively modify only the targeted receptor, thereby reducing non-specific reactions and decreasing the probability of toxic side effects.

The term "a peptide having a sidechain modified by" a moiety, as used herein, refers to a peptide (or peptide mimetic, see below) in which at least one residue has a sidechain comprising that moiety. Thus, for example, a "peptide having a sidechain modified by a dipolar moiety" means a peptide in which at least one side chain comprises a dipolar moiety.

The LHRH antagonist peptides of the present invention also include peptide analogs and peptide mimetics. The term "peptide compound" as used herein is intended to encompass peptides, peptide analogs, peptide derivatives and peptide mimetics. The terms "peptide analog", "peptide derivative" and "peptide mimetic" as used herein are intended to include molecules which mimic the chemical structure of a peptide and retain the functional properties of the peptide. A "residue" refers to an amino acid or amino acid mimetic incorporated in the peptide compound by an amide bond or amide bond mimetic. Approaches to designing peptide analogs are known in the art. For example, see Farmer, P. S. in *Drug Design* (E. J. Ariens, ed.) Academic Press, New York, 1980, vol. 10, pp. 119–143; Ball. J. B. and Alewood, P. F. (1990) *J. Mol. Recognition* 3:55; Morgan, B. A. and Gainor, J. A. (1989) *Ann. Rep. Med Chem.* 24:243; and Freidinger, R. M. (1989) *Trends Pharmacol. Sci.* 10:270.

An "amino acid mimetic" refers to a moiety, other than a naturally occurring amino acid, that conformationally and functionally serves as a substitute for a particular amino acid in a peptide compound without adversely interfering to a significant extent with the function of the peptide (e.g., interaction of the peptide with an LHRH receptor). In some circumstances, substitution with an amino acid mimetic may actually enhance properties of the peptide (e.g., interaction of the peptide with an LHRH receptor). Examples of amino acid mimetics include D-amino acids. LHRH antagonist peptides substituted with one or more D-amino acids may be made using well known peptide synthesis procedures. The effect of amino acid substitutions with D-amino acids or other amino-acid mimetics can be tested using assays, e.g., the AOA and histamine-release assays as described below. Other methods of determining the effect of substitution with an amino acid mimetic will be apparent to the skilled artisan.

The peptide analogs or mimetics of the invention include isosteres. The term "isostere" as used herein refers to a sequence of two or more residues that can be substituted for a second sequence because the steric conformation of the first sequence fits a binding site specific for the second sequence. The term specifically includes peptide back-bone modifications (i.e., amide bond mimetics) well known to those skilled in the art. Such modifications include modifications of the amide nitrogen, the α-carbon, amide carbonyl, complete replacement of the amide bond, extensions, deletions or backbone crosslinks. Several peptide backbone modifications are known, including ψ[CH$_2$S], ψ[CH$_2$NH)], ψ[C(S)NH$_2$], ψ[NHCO], ψ[C(O)CH$_2$], and ψ[(E) or (Z) CH=CH]. In the nomenclature used above, ψ indicates the absence of an amide bond. The structure that replaces the amide group is specified within the brackets. Other examples of isosteres include peptides substituted with one or more benzodiazepine molecules (see e.g., James, G. L. et al. (1993) *Science* 260:1937–1942)

Other possible modifications include an N-alkyl (or aryl) substitution (ψ[CONR]), backbone crosslinking to construct lactams and other cyclic structures, or retro-inverso amino acid incorporation (ψ[NHCO]). By "inverso" is meant replacing L-amino acids of a sequence with D-amino acids, and by "retro-inverso" or "enantio-retro" is meant reversing the sequence of the amino acids ("retro") and replacing the L-amino acids with D-amino acids. For example, if the parent peptide is Thr-Ala-Tyr, the retro modified form is Tyr-Ala-Thr, the inverso form is thr-ala-tyr, and the retro-inverso form is tyr-ala-thr (lower case letters refer to D-amino acids). Compared to the parent peptide, a retro-inverso peptide has a reversed backbone while retaining substantially the original spatial conformation of the side chains, resulting in a retro-inverso isomer with a topology that closely resembles the parent peptide and is able to bind the selected LHRH receptor. See Goodman et al. "Perspectives in Peptide Chemistry" pp. 283–294 (1981). See also U.S. Pat. No. 4,522,752 by Sisto for further description of "retro-inverso" peptides.

In addition to amino acid-substituted LHRH antagonist peptides, the invention also encompasses LHRH antagonist peptide compounds having other modifications. For example, the amino-terminus or carboxy-terminus of the peptide can be modified. The term "amino-derivative group" is intended to include amino-terminal modifications of the peptide compounds of the invention. Examples of N-terminal modifications include alkyl, cycloalkyl, aryl, arylalkyl, and acyl groups. A preferred N-terminal modification is acetylation. The N-terminal residue may be linked to a variety of moieties other than amino acids such as polyethylene glycols (such as tetraethylene glycol carboxylic acid monomethyl ether), pyroglutamic acid, succinoyl, methoxy succinoyl, benzoyl, phenylacetyl, 2-, 3-, or 4-pyridylalkanoyl, aroyl, alkanoyl (including acetyl and cycloalkanoyl e.g., cyclohexylpropanoyl), arylalkanoyl, arylaminocarbonyl, alkylaminocarbonyl, cycloalkylaminocarbonyl, alkyloxycarbonyl (carbamate caps), and cycloalkoxycarbonyl, among others.

The term "carboxy-derivative group" is intended to include carboxy-terminal modifications of the peptide compounds of the invention. Examples of modifications of the C-terminus include modification of the carbonyl carbon of the C-terminal residue to form a carboxyterminal amide or alcohol (i.e., a reduced form). In general, the amide nitrogen, covalently bound to the carbonyl carbon on the C-terminal residue, will have two substitution groups. each of which can be hydrogen, alkyl or an alkylaryl group (substituted or unsubstituted). Preferably the C-terminal is an amido group, such as —CONH$_2$, —CONHCH$_3$, —CONHCH$_2$C$_6$H$_5$ or —CON(CH$_3$)$_2$, most preferably —CONH$_2$, but may also be 2-, 3-, or 4-pyridylmethyl, 2-, 3-, or 4-pyridylethyl, carboxylic acid, ethers, carbonyl esters, alkyl, arylalkyl, aryl, cyclohexylamide, piperidineamide, other mono or disubstituted amides, ureas, or carbamates. Other moieties that can be linked to the C-terminal residue include piperidine-4-carboxylic acid or amide and cis- or trans-4-aminocyclohexanecarboxylic acid or amide.

The modified forms of LHRH antagonist peptides of the invention, including L- or D-amino acid substitutions, covalent modification of end termini or side chains, and peptide analogs and mimetics can be selected for desired alterations of the physical or chemical properties of the peptide, for example, increased stability, solubility, bioavailability, increased or decreased immunogenicity, etc. The peptides of the invention can be targeted to particular organs (e.g. the brain) by methods known in the art, for example, the dihydropyridine-pyridinium carrier of Bodor (see, e.g., U.S. Pat. No. 4,540,564). In an exemplary embodiment, when a side-chain modified by a pyridinium moiety is desired, the corresponding N-alkylated dihydropyridine sidechain is incorporated into the peptide. When the peptide is administered to a subject, the N-alkylated dihydropyridine sidechain is oxidized in vivo to the desired pyridinium moiety.

Preferred LHRH antagonist peptides of the present invention range in length from about 8 to about 12 residues, more preferably from 9 to 11 residues, and most preferably are 10 residues in length.

The LHRH antagonist peptides of the present invention can be prepared by any suitable method for peptide synthesis, including solution-phase and solid-phase chemical synthesis. Preferably, the peptides are synthesized on a solid support. Methods for chemically synthesizing peptides are well known in the art (see, e.g., Bodansky, M. *Principles* of *Peptide Synthesis*, Springer Verlag, Berlin (1993) and Grant, G. A (ed.). *Synthetic Peptides: A User's Guide*, W. H. Freeman and Company, New York (1992). Automated peptide synthesizers are commercially available.

The use of combinatorial libraries to identify ligands is now well established (see, e.g., M. A. Gallop et al., (1994) *J. Med. Chem.* 37:1233; and E. M. Gordon et al., (1994) *J. Med. Chem.* 37:1385; and references cited therein). Therefore, LHRH antagonist peptides can be identified by chemical (e.g., solution or solid-phase) synthesis of combinatorial libraries (e.g., of peptides or peptoids) and screening of the resulting libraries according to known techniques. Thus, many potential ligands can be synthesized and screened in a short period of time, and the most active ligands selected for further testing or use.

Standard abbreviations and conventions are used throughout this disclosure when describing the peptides of the invention. Peptides are written with the N-terminus on the left, the carboxyl terminus on the right. Amino acids are of the L-form unless stated otherwise, e.g., D-Lys means the D-form of lysine. Ac-Xaa means the N-terminal residue Xaa is N-acetylated; C-terminal amides are denoted Xaa-NH$_2$ In Table 1, only residues which differ from native mammalian LHRH are noted; thus, the notation Met(S$^+$Me)$^8$-LHRH.TFA means a peptide which differs from native mammalian LHRH only in the substitution of Met(S$^+$Me) for the native Arg at position 8 (TFA indicates the trifluoroacetate salt). Lys(iPr) denotes N-ε-2-propyl-lysinyl; other alkylating and acylating moieties are similar indicated. Thus, for example, Met(S+CH$_2$C$_6$H$_5$) denotes S-benzyl methionine. Certain other non-standard residues and moieties are abbreviated as follows:

| Abbreviation | Residue or moiety |
|---|---|
| pGlu | pyro-glutamyl |
| Nal | 3-(2-naphthyl)alaninyl |
| Ada | 3-(1-adamantanyl)alaninyl |
| 4-Cl-Phe | (4'-chlorophenyl)alaninyl |
| Qal | 3-(2'quinolinyl)alaninyl |
| Pal | 3-(3'-pyridyl)alaninyl |
| Pal(N—O) | 3-(3'-pyridine-N-oxide)alaninyl |
| Pal(iPr) | 3-(N-(2-propyl)-3'-pyridinium)alaninyl |
| Pal(Bzl) | 3-(N-(benzyl)-3'-pyridinium)alaninyl |
| Pal(CH$_2$COO$^-$) | 3-(3'-pyridinium-N-(2-acetate))alaninyl |
| Lys(iPr) | N-ε-2-propyl-lysinyl |
| Imdac | 2-oxo-4-imidazolinyl |
| Otac | 2-oxo-4-thiazolinyl |
| Ppic | 3-(piperidin-1-yl-propanoyl |
| Dodac | 2,5-dioxo-4-imidazolinyl |
| Met(S$^+$Me) | S-methyl methioninyl |
| PEG | polyethylene glycol |
| Cit | citrullinyl |
| Hci | homocitrullinyl |
| Glu(Taurine) | 5-(2-sulfoethylamido)glutamyl |
| Pyz | 1,4-pyrazinecarbonyl |
| Pip | pipecolyl |
| CNa | (2-cyano)acetyl |
| Dea | diethylamide |
| Onic | 3-nicotinyl-N-oxide |
| Glc | gluconate |
| Orotic | orotate |
| Orn | ornithine |
| Dap | 2,4-diaminopropionyl |

I. LHRH Antagonist Peptides of the Invention

In one aspect, the invention pertains to LHRH antagonist peptides.

In one embodiment, the invention provides an LHRH antagonist comprising a peptide compound, wherein a residue of the peptide compound corresponding to the amino acid at position 6 of natural mammalian LHRH comprises D-Lys(Imdac), D-Lys(Ppic), D-Lys(Dodac), D-Lys(pGlu), D-Lys(Otac) and D-Lys(Onic) or a moiety selected from the group consisting of a dipolar moiety, a sulfonium moiety, a receptor-modifying moiety and a small polar moiety, such that the peptide compound has LHRH antagonist activity, with the provisos that the dipolar moiety is not a zwitterionic pyridinium and the residue is not D-Cit, D-Hci or a lower alkyl derivative of D-Cit or D-Hci. Preferably, the peptide compound comprises about 8 to about 12 residues. More preferably, the peptide compound comprises 10 residues.

In another embodiment, the invention provides a peptide compound comprising a structure:

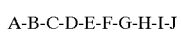

wherein
A is pyro-Glu, Ac-D-Nal, Ac-D-Qal, Ac-Sar, or Ac-D-Pal;
B is His or 4-Cl-D-Phe;
C is Trp, D-Pal, D-Nal, L-Nal, D-Pal(N—O), or D-Trp;
D is Ser;
E is N-Me-Ala, Tyr, N-Me-Tyr, Ser, Lys(iPr), 4-Cl-Phe, His, Asn, Met, Ala, Arg or Ile;
F is D-Lys(lmdac), D-Lys(Ppic), D-Lys(Dodac), D-Lys(pGlu), D-Lys(Otac), D-Lys(Onic) or a structure:

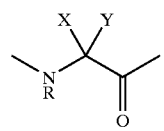

wherein
R and X are, independently, H or alkyl; and
Y comprises a moiety selected from the group consisting a dipolar moiety, a sulfonium moiety, a receptor-modifying moiety and a small polar moiety, the provisos that the dipolar moiety is not a zwitterionic pyridinium and F is not D-Cit, D-Hci or a lower alkyl derivative of D-Cit or D-Hci;
G is Leu or Trp;
H is Lys(iPr), Gln, Met, or Arg;
I is Pro; and
J is Gly-NH$_2$ or D-Ala-NH$_2$;
or a pharmaceutically acceptable salt thereof.

In a subembodiment, Y comprises a dipolar moiety, with the proviso that the dipolar moiety is not a zwitterionic pyridinium. Preferred dipolar moieties include ylids, tertiary amine oxides, nitrile oxides and pyridine-N-oxides.

In another subembodiment, Y comprises a sulfonium moiety.

In another subembodiment, Y comprises a receptor-modifying moiety. Preferred receptor modifying moieties include ylids, sulfonium moieties, α-halocarbonyls, sulfates, sulfonates, alkyl halides and benzyl halides.

In another subembodiment, F is D-Lys(Imdac), D-Lys(Ppic) and D-Lys(Dodac), D-Lys(pGlu), D-Lys(Otac) or D-Lys(Onic).

In another subembodiment, Y comprises a small polar moiety, with the proviso that F is not D-Cit, D-Hci or a lower alkyl derivative of D-Cit or D-Hci. Preferably, F is selected from the group consisting of D-Asn, D-Gln and D-Thr. More preferably, F is D-Asn.

In another embodiment, the invention provides an LHRH antagonist comprising a peptide compound, wherein a residue of the peptide compound corresponding to the amino acid at position 6 of natural mammalian LHRH comprises a small polar moiety such that the peptide compound has LHRH antagonist activity, with the proviso that the residue is not D-Cit, D-Hci or a lower alkyl derivative of D-Cit or D-Hci. Preferably, the antagonist has an antiovulatory activity of less than about 1 µg per rat in a rat antiovulation assay and/or the antagonist has an $ED_{50}$ in a histamine release assay of at least about 5 µg/ml. Preferably, the peptide compound comprises about 8 to about 12 residues. More preferably, the peptide compound comprises 10 residues.

In another embodiment, the invention provides a peptide compound comprising a structure:

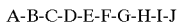

wherein
A is pyro-Glu, Ac-D-Nal, Ac-D-Qal, Ac-Sar, or Ac-D-Pal
B is His or 4-Cl-D-Phe
C is Trp, D-Pal, D-Nal, L-Nal, D-Pal(N—O), or D-Trp
D is Ser
E is N-Me-Ala, Tyr, N-Me-Tyr, Ser, Lys(iPr), 4-Cl-Phe, His, Asn, Met, Ala, Arg or Ile;
F is

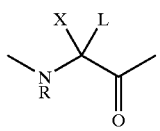

wherein
R and X are, independently, H or alkyl; and
L comprises a small polar moiety, with the proviso that F is not D-Cit, D-Hci or a lower alkyl derivative of D-Cit or D-Hci;
G is Leu or Trp;
H is Lys(iPr), Gln. Met, or Arg
I is Pro; and
J is Gly-NH$_2$ or D-Ala-NH$_2$;
or a pharmaceutically acceptable salt thereof. Preferably, F is selected from the group consisting of D-Asn. D-Gln and D-Thr.

In another embodiment, the invention provides a peptide compound comprising a structure:

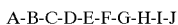

wherein
A is pyro-Glu, Ac-D-Nal, Ac-D-Qal, Ac-Sar, or Ac-D-Pal;
B is His or 4Cl-D-Phe;
C is Trp, D-Pal, D-Nal, L-Nal, D-Pal(N—O), or D-Trp;
D is Ser;
E is N-Me-Ala, Tyr, N-Me-Tyr, Ser, Lys(iPr), 4-Cl-Phe, His, Asn, Met, Ala, Arg or Ile;
F is D-Asn;
G is Leu or Trp;
H is Lys(iPr), Gln, Met, or Arg;
I is Pro; and
J is Gly-NH$_2$ or D-Ala-NH$_2$;
or a pharmaceutically acceptable salt thereof.

In another embodiment, the invention provides a peptide compound comprising a structure:

wherein
A is pyro-Glu, Ac-D-Nal, Ac-D-Qal, Ac-Sar, or Ac-D-Pal;
B is His or 4-Cl-D-Phe;
C is Trp, D-Pal, D-Nal, L-Nal, D-Pal(N—O), or D-Trp;
D is Ser;
E is N-Me-Ala, Tyr, N-Me-Tyr, Ser, Lys(iPr), 4-Cl-Phe, His, Asn, Met, Ala, Arg or Ile;
F is D-Arg, D-Lys(iPr), D-Pal(iPr), D-Cit or Q, wherein Q has a structure

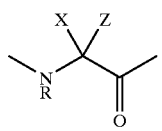

wherein
R and X are, independently, H or alkyl; and
Z comprises a sulfonium moiety;
G is Leu or Trp;
H is Lys(iPr), Gln, Met, Arg or Q;
I is Pro; and
J is Gly-NH$_2$ or D-Ala-NH$_2$;
with the proviso that at least one of F and H is Q;
or a pharmaceutically acceptable salt thereof.

In preferred specific embodiments, the invention provides peptide compounds of the following structures:

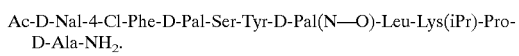

and pharmaceutically acceptable salts thereof.

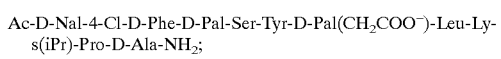

and pharmaceutically acceptable salts thereof.

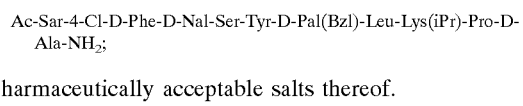

and pharmaceutically acceptable salts thereof.

and pharmaceutically acceptable salts thereof.

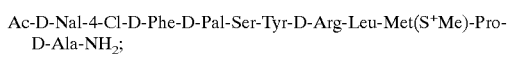

and pharmaceutically acceptable salts thereof.

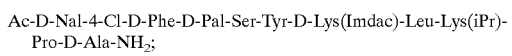

and pharmaceutically acceptable salts thereof.

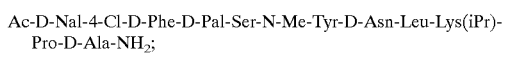

and pharmaceutically acceptable salts thereof.

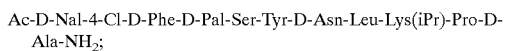

and pharmaceutically acceptable salts thereof.

In another embodiment, the invention provides a peptide comprising a structure:

A-B-C-D-E-F-G-H-I-J wherein
- A is pyro-Glu, Ac-D-Nal, Ac-D-Qal, Ac-Sar, or Ac-D-Pal
- B is His or 4-Cl-D-Phe
- C is Trp, D-Pal, D-Nal, L-Nal-D-Pal(N—O), or D-Trp
- D is Ser
- E is N-Me-Ala, Tyr, N-Me-Tyr, Ser, Lys(iPr), 4-Cl-Phe, His, Asn, Met, Ala, Arg or Ile;
- F is

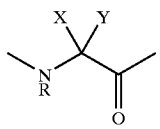

wherein
- R and X are, independently, H or alkyl; and
- Y comprises a dipolar moiety;
- G is Leu or Trp;
- H is Lys(iPr), Gln, Met, or Arg
- I is Pro; and
- J is Gly-NH$_2$ or D-Ala-NH$_2$;

or a pharmaceutically acceptable salt thereof. In preferred embodiments, Y is selected from the group consisting of ylids, tertiary amine oxides, nitrile oxides, pyridine-N-oxides, and pyridinium zwitterions. In particularly preferred embodiments, Y is an ylid, a pyridine-N-oxide or a pyridinium zwitterion.

In another aspect, the invention provides a peptide comprising a structure:

A-B-C-D-E-F-G-H-I-J wherein
- A is pyro-Glu, Ac-D-Nal, Ac-D-Qal, Ac-Sar, or Ac-D-Pal
- B is His or 4-Cl-D-Phe
- C is Trp, D-Pal, D-Nal, L-Nal-D-Pal(N—O), or D-Trp
- D is Ser
- E is N-Me-Ala, Tyr, N-Me-Tyr, Ser, Lys(iPr), 4-Cl-Phe, His, Asn, Met, Ala, Arg or Ile;
- F is D-Arg, D-Lys(iPr), D-Pal(iPr), D-Cit or Q, wherein Q has a structure

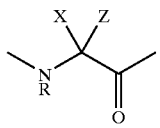

wherein
- R and X are, independently, H or alkyl; and
- Z comprises a cationic moiety selected from the group consisting of cationic pyridinium moieties and sulfonium moieties, with the proviso that the cationic moiety is not N-methyl pyridinium;
- G is Leu or Trp;
- H is Lys(iPr), Gln, Met, Arg or Q;
- I is Pro; and
- J is Gly-NH$_2$ or D-Ala-NH$_2$;

with the proviso that at least one of F and H is Q; or a pharmaceutically acceptable salt thereof.

In preferred embodiments, F is Q and Z is a cationic pyridinium moiety. In preferred embodiments, Z is an N-benzyl pyridinium moiety. In other preferred embodiments, F is Q and Z is a sulfonium moiety. In yet other preferred embodiments, H is Q and Z is a sulfonium moiety.

In another aspect, the invention provides a peptide comprising a structure:

A-B-C-D-E-F-G-H-I-J wherein
- A is p-Glu, Ac-D-Nal, Ac-D-Qal, Ac-Sar, or Ac-D-Pal
- B is His or 4-Cl-D-Phe
- C is Trp, D-Pal, D-Nal, L-Nal-D-Pal(N—O), or D-Trp
- D is Ser
- E is N-Me-Ala, Tyr, N-Me-Tyr, Ser, Lys(iPr), 4-Cl-Phe, His, Asn, Met, Ala, Arg or Ile;
- F is

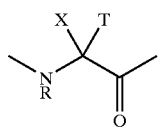

wherein
- R and X are, independently, H or alkyl; and
- T comprises a receptor-modifying moiety;
- G is Leu or Trp;
- H is Lys(iPr), Gin, Met, or Arg
- I is Pro; and
- J is Gly-NH$_2$ or D-Ala-NH$_2$;

or a pharmaceutically acceptable salt thereof.

In preferred embodiments, T is selected from the group consisting of ylids, sulfonium moieties, α-halocarbonyls, sulfates, sulfonates, alkyl halides and benzyl halides. In a particularly preferred embodiment, T is an α-halocarbonyl.

In another embodiment, the invention provides a peptide comprising a structure:

A-B-C-D-E-F-G-H-I-J wherein
- A is pyro-Glu, Ac-D-Nal, Ac-D-Qal, Ac-Sar, or Ac-D-Pal
- B is His or 4-Cl-D-Phe
- C is Trp, D-Pal. D-Nal, L-Nal-D-Pal(N—O), or D-Trp
- D is Ser
- E is N-Me-Ala, Tyr, N-Me-Tyr, Ser, Lys(iPr), 4-Cl-Phe, His, Asn, Met, Ala, Arg or Ile;
- F is

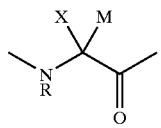

wherein
- R and X are, independently, H or alkyl; and
- M comprises an N-acyl hydrophilic moiety;
- G is Leu or Trp;
- H is Lys(iPr), Gln, Met, or Arg
- I is Pro; and J is Gly-NH$_2$ or D-Ala-NH$_2$;
or a pharmaceutically acceptable salt thereof.

In another aspect, the invention provides a peptide comprising a structure:

A-B-C-D-E-F-G-H-I-J wherein
A is pyro-Glu, Ac-D-Nal, Ac-D-Qal, Ac-Sar, or Ac-D-Pal
B is His or 4-Cl-D-Phe
C is Trp, D-Pal, D-Nal, L-Nal-D-Pal(N—O), or D-Trp
D is Ser
E is N-Me-Ala, Tyr, N-Me-Tyr, Ser, Lys(iPr), 4-Cl-Phe, His, Asn, Met, Ala, Arg or Ile;
F is

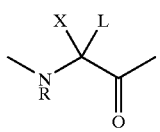

wherein
R and X are, independently, H or alkyl; and
L comprises a small polar moiety;
G is Leu or Trp;
H is Lys(iPr), Gln, Met, or Arg
I is Pro; and
J is Gly-NH$_2$ or D-Ala-NH$_2$;
or a pharmaceutically acceptable salt thereof.

In another aspect, the invention provides an LHRH antagonist, comprising a peptide having a sidechain modified by a dipolar moiety forming a modified peptide, such that the modified peptide has LHRH antagonist activity. In preferred embodiments, the dipolar moiety is selected from the group consisting of ylids, tertiary amine oxides, nitrile oxides, pyridine-N-oxides, and pyridinium zwitterions. In more preferred embodiments, the dipolar moiety is an ylid, a pyridine-N-oxide or a pyridinium zwitterion. In other preferred embodiments, the peptide comprises about 8 to about 12 residues. In more preferred embodiments, the peptide comprises 10 residues. In certain preferred embodiments, the dipolar moiety modifies residue 6. In certain preferred embodiments, the LHRH antagonist is a peptide mimetic.

In another embodiment, the invention provides an LHRH antagonist, comprising a peptide having a sidechain modified by a cationic moiety selected from the group consisting of cationic pyridinium moieties and sulfonium moieties, with the proviso that the cationic moiety is not N-methyl pyridinium, forming a modified peptide, such that the modified peptide has LHRH antagonist activity. In preferred embodiments, the cationic moiety is a cationic pyridinium moiety. In other preferred embodiments, the cationic moiety is a sulfonium moiety. In other preferred embodiments, the peptide comprises about 8 to about 12 residues. In more preferred embodiments, the peptide comprises 10 residues. In other preferred embodiments, the cationic moiety modifies at least one of residue 6 and residue 8. In other preferred embodiments, the LHRH antagonist is a peptide mimetic.

In another embodiment, the invention provides an LHRH antagonist, comprising a peptide having a sidechain modified by a receptor-modifying moiety forming a modified peptide, such that the modified peptide has LHRH antagonist activity. In preferred embodiments, the receptor-modifying moiety is selected from the group consisting of ylids, sulfonium moieties, α-halocarbonyls, sulfates, sulfonates alkyl halides, and benzyl halides. In preferred embodiments, the peptide comprises about 8 to 12 residues. In more preferred embodiments, the peptide comprises 10 residues. In preferred embodiments, the receptor-modifying moiety modifies residue 6. In preferred embodiments, the LHRH antagonist is a peptide mimetic.

In another embodiment, the invention provides an LHRH antagonist, comprising a peptide having a sidechain modified by a hydrophilic N-acyl moiety forming a modified peptide, such that the modified peptide has LHRH antagonist activity. In preferred embodiments, the hydrophilic N-acyl moiety modifies position 6. In preferred embodiments, a residue comprises a hydrophilic acyl moiety is selected from the group consisting of D-Lys(Imdac), D-Lys(Ppic), and D-Lys(Dodac). In preferred embodiments, the hydrophilic N-acyl moiety has a log P between −1 and +2.

In another embodiment, the invention provides an LHRH antagonist, comprising a peptide having a small polar moiety in position 6, such that the peptide has LHRH antagonist activity. In preferred embodiments, the antagonist has an AOA less than about 1 μg. In preferred embodiments, the antagonist has a histamine-releasing activity of at least about 5 μg.

II. Pharmaceutical Compositions

The LHRH antagonist peptides of the invention can be incorporated into pharmaceutical compositions suitable for administration to a subject. In a preferred embodiment, the pharmaceutical composition comprises an LHRH antagonist peptide of the invention and a pharmaceutically acceptable carrier.

A "therapeutically effective amount" refers to an amount effective, at dosages and for periods of time necessary, to achieve the desired result. A therapeutically effective amount of an LHRH antagonist peptide of the present invention may vary according to factors such as the disease state, age, sex, and weight of the individual, and the ability of the antagonist to elicit a desired response in the individual. Dosage regimens may be adjusted to provide the optimum therapeutic response. A therapeutically effective amount is also one in which any toxic or detrimental effects of the antagonist are outweighed by the therapeutically beneficial effects. A non-limiting range for a therapeutically effective amount of an LHRH antagonist is 0.01 μg/kg-10 mg/kg, preferably between about 0.01 and 5 mg/kg. It is to be noted that dosage values may vary with the severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous or parenteral administration (e.g., by injection). Depending on the route of administration, the active compound may be coated in a material to protect the compound from the action of acids and other natural conditions which may inactivate the compound.

A "pharmaceutically acceptable salt" refers to a salt that retains the desired biological activity of the parent compound and does not impart any undesired toxicological effects. Examples of such salts are salts of acids such as hydrochloric acid, hydrobromic acid, sulfuric acid, phosporic acid, nitric acid, and the like; acetic acid, oxalic acid, tartaric acid, succinic acid, malic acid, benzoic acid, pamoic acid, alginic acid, methanesulfonic acid, naphthalenesulfonic acid, and the like. Also included are salts of cations such as sodium, potassium, lithium, zinc, copper, barium, bismuth, calcium, and the like; or organic cations such as trialkylammonium. Combinations of the above salts are also useful.

An LHRH-R antagonist can be administered by a variety of methods known in the art. In a preferred embodiment, the LHRH-R antagonist is administered in a time release formulation, for example in a composition which includes a slow release polymer, or by depot injection. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978. Particularly preferred formulations include controlled-release compositions such as are known in the art for the administration of leuprolide (trade name: Lupron®), e.g., microcapsules (U.S. Pat. Nos. 4,652,441 and 4,917,893), injectable formulations (U.S. Pat. No. 4,849,228), lactic acid-glycolic acid copolymers useful in making microcapsules or injectable formulations (U.S. Pat. Nos. 4,677,191 and 4,728,721), and sustained-release compositions for water-soluble polypeptides (U.S. Pat. No. 4,675,189).

When appropriately formulated, an LHRH-R antagonist may be orally administered, for example, with an inert diluent or an assimilable edible carrier. The LHRH antagonists and other ingredients may also be enclosed in a hard or soft shell gelatin capsule, compressed into tablets, or incorporated directly into the subject's diet. For oral therapeutic administration, the LHRH antagonists may be incorporated with excipients and used in the form of ingestible tablets, buccal tablets, troches, capsules, elixirs, suspensions, syrups, wafers, and the like. The percentage of the LHRH antagonists in the compositions and preparations may, of course, be varied. The amount of the LHRH antagonists in such therapeutically useful compositions is such that a suitable dosage will be obtained.

To administer the LHRH antagonists by other than parenteral administration, it may be necessary to coat the compound with, or co-administer the compound with, a material to prevent its inactivation. For example, the LHRH antagonists may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., (1984) *J. Neuroimmunol.* 7:27). Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as manitol, sorbitol, or sodium chloride in the composition. Prolonged absorption of the injectable compositions can be brought about by including in the composition an agent which delays absorption, for example, monostearate salts and gelatin.

Sterile injectable solutions can be prepared by incorporating the active compound (e.g., LHRH antagonist) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

III. Methods of Using the LHRH Antagonists of the Invention

The LHRH antagonist peptides of the present invention are useful for the treatment of such conditions as precocious puberty, prostate cancer, ovarian cancer, benign prostatic hypertrophy, endometriosis, uterine fibroids, breast cancer, premenstrual syndrome, polycystic ovary syndrome, and diseases which result from excesses of gonadal hormones in humans or animals of either sex. The LHRH antagonist peptides of the invention are also useful for behavior modification (e.g., "chemical castration"). The LHRH antagonist peptides are also useful for controlling reproduction in both males and females. Furthermore, the peptides of the invention may be used to treat immunosuppressed patients, as described in, for example, U.S. Pat. No. 5,003,011.

Thus, in one embodiment, the invention provides a method of inhibiting LHRH activity in a subject, comprising administering to a subject an effective amount of an LHRH antagonist of the present invention, such that LHRH activity is inhibited.

In another embodiment, the invention provides a method of inhibiting LHRH activity in a cell, comprising contacting a cell with an LHRH antagonist of the invention, such that LHRH activity is inhibited.

In another embodiment, the invention provides a method of inhibiting growth of a hormone-dependent tumor in a subject, comprising administering to a subject an effective amount of an LHRH antagonist of the invention, such that tumor growth is inhibited. In a preferred embodiment, an LHRH antagonist of the invention is administered to a subject suffering from prostate cancer to inhibit the growth of the prostatic tumor.

In another embodiment, the invention provides a method of inhibiting ovulation in a subject, comprising administering to a subject an effective amount of an LHRH antagonist of the invention, such that ovulation is inhibited.

In another aspect, the invention provides a packaged formulation for treating a subject for a disorder associated with LHRH activity, comprising an LHRH antagonist of the invention packaged with instructions for using the LHRH antagonist for treating a subject having a disorder associated with LHRH activity.

In another aspect, the invention encompasses use of the peptide compounds of the invention in the manufacture of a medicament for the treatment of a disorder in which inhibition of LHRH activity is beneficial. For example, the disorder in which inhibition of LHRH activity is beneficial can be selected from the group consisting of precocious puberty, prostate cancer, ovarian cancer, benign prostatic hypertrophy, endometriosis, uterine fibroids, breast cancer, premenstrual syndrome, polycystic ovary syndrome, and diseases which result from excesses of gonadal hormones.

This invention is further illustrated by the following examples which should not be construed as limiting. The contents of all references, patents and published patent applications cited throughout this application are hereby incorporated by reference.

In the examples, the following abbreviations are used:

Boc: N-t-butoxycarbonyl

HOBt: 1-hydroxybenzotriazole

MCPBA: m-chloroperbenzoic acid

DCC: dicyclohexylcarbodiimide

EXAMPLE 1

Anti-Ovalulatory and Histamine Release Activity of LHRH Antagonists

Anti-ovulatory activity (AOA) was measured by an in vivo assay in rats, as described in Corbin and Beattie, *Endocrine Res. Commun.* 2:1 (1975). In brief, female rats are injected with a candidate LHRH antagonist on the day of proestrus; in general, the candidate LHRH antagonist was dissolved in 0.1% DMSO. The ability of the candidate peptide to inhibit ovulation is measured by determining the number of rats which ovulate. A candidate peptide is considered to have LHRH antagonist qualities if it inhibits ovulation in as least 50% of the treated rats at a dose of 5 µg per rat. Preferred LHRH antagonists inhibit ovulation in at least 50% of rats at a dose of 2 µg per rat, more preferably at a dose of 1 µg per rat, and still more preferably at a dose of 0.5 µg per rat.

Histamine-releasing activity was assayed by the method described in U.S. Pat. No. 4,851,385 to Roeske. Briefly, a suspension of rat mast cells was added to increasing concentration of an LHRH antagonist peptide and incubated for 15 minutes at 37° C. The buffer contained 25 mM PIPES, pH 7.4, NaCl (119 mM), KCl (5 mM), NaOH (40mM) glucose (5.6 M), $CaCl_2$ (1 mM) and 0.1% bovine serum albumin. The reaction was stopped by centrifugation at 400×g for 15 minutes at 4° C., and the supernatant assayed for histamine content by a published method (Siriganian (1974) *Anal. Biochem.* 57:383 and Siriganian and Hook (1986) in "Manual of Clinical Immunology", 3rd ed., N. R. Rose, H. Friedman, and J. L Fahey, eds., p. 808), or by a manual method which gave similar results. Maximal histamine release occurred rapidly, typically in less than one minute. No evidence of cell toxicity was seen for any of the peptides tested. The histamine-releasing activity of peptides is measured as the $ED_{50}$, in gg/ml; a higher $ED_{50}$ represents lower histamine release.

The AOA and histamine-releasing activities of several peptides are summarized in Table 1.

TABLE 1

LHRH Antagonists

| Com-pound | Sequence | AO activity (AOA) | Histamine release |
|---|---|---|---|
| 3341 | Ac-D-Nal$^1$,4-Cl-D-Phe$^2$,D-Pal$^3$, D-Gln$^6$-Lys(iPr)$^8$, D-Ala$^{10}$-LHRH.TFA | 4/10 @ 1 µg 2/10 @ 2 µg | 106 |
| 3342 | Ac-D-Nal$^1$,4-Cl-D-Phe$^2$,D-Pal$^3$, D-Asn$^6$-Lys(iPr)$^8$, D-Ala$^{10}$-LHRH.TFA | 2/10 @ 2 µg | 126 |
| 3343 | Ac-D-Nal$^1$,4-Cl-D-Phe$^2$,D-Pal$^3$, D-Thr$^6$-Lys(iPr)$^8$, D-Ala$^{10}$-LHRH.TFA | 5/10 @ 1 µg | 62 |
| 3344 | Ac-D-Nal$^1$,4-Cl-D-Phe$^2$,D-Pal$^3$, D-Cit$^6$-Lys(iPr)$^8$, Pip$^9$-D-Ala$^{10}$-LHRH.TFA | 9/10 @ 1 µg | 32 |
| 3361 | Ac-D-Nal$^1$,4-Cl-D-Phe$^2$,D-Pal$^3$, D-Glu(Taurine)$^6$-Lys(iPr)$^8$,D-Ala$^{10}$-LHRH.TFA | 1/8 @ 5 µg | 131 |
| 3362 | Ac-D-Nal$^1$,4-Cl-D-Phe$^2$,D-Pal$^3$, D-Cit$^6$-Lys(iPr)$^8$-LHRH.TFA | 4/8 @ 1 µg | 22 |
| 3363 | Ac-D-Nal$^1$,4-Cl-D-Phe$^2$,D-Pal$^3$, D-Cit$^6$-Lys(iPr)$^8$,Pip$^9$-LHRH.TFA | 6/8 @ 1 µg | 25 |
| 3364 | Ac-D-Nal$^1$,4-Cl-D-Phe$^2$,D-Pal$^3$, D-Phe(4-NO$_2$)$^6$-Lys(iPr)$^8$, D-Ala$^{10}$-LHRH.TFA | 6/8 @ 1 µg | 14 |
| 3365 | Ac-D-Nal$^1$,4-Cl-D-Phe$^2$,D-Pal$^3$, D-Cit$^6$-Lys(iPr)$^8$, ProNHEt$^9$-des-Gly$^{10}$-LHRH.TFA | | 24 |
| 3366 | Ac-D-(or L)-9-anthryl-Ala$^1$, 4-Cl-D-Phe$^2$,D-Pal$^3$, D-Cit$^6$-Lys(iPr)$^8$, D-Ala$^{10}$-LHRH.TFA | 6/8 @ 5 µg | |
| 3367 | Ac-L-(or D)-9-anthryl-Ala$^1$, D-Pal$^3$,D-Cit$^6$-Lys(iPr)$^8$, D-Ala$^{10}$-LHRH.TFA | 7/8 @ 5 µg | |
| 3368 | Ac-D-(or L)-Ada-Ala$^1$,4-Cl-D-Phe$^2$, D-Pal$^3$,D-Cit$^6$-Lys(iPr)$^8$, D-Ala$^{10}$-LHRH.TFA | 5/8 @ 5 µg | 34 |
| 3369 | Ac-L-(or D)-Ada-Ala$^1$,4-Cl-D-Phe$^2$, D-Pal$^3$,D-Cit$^6$-Lys(iPr)$^8$, D-Ala$^{10}$-LHRH.TFA | 7/8 @ 5 µg | 93 |

TABLE 1-continued

LHRH Antagonists

| Compound | Sequence | AO activity (AOA) | Histamine release |
|---|---|---|---|
| 3423A | Ac-D-Nal$^1$,4-Cl-D-Phe$^2$,D-Pal$^3$, D-Lys(Glc)$^6$-Lys(iPr)$^8$, D-Ala$^{10}$-LHRH.TFA | 7/10 @ 0.5 μg 2/10 @ 1 μg 0/10 @ 2 μg | 52 |
| 3428 | Ac-D-Nal$^1$,4-Cl-D-Phe$^2$,D-Pal$^3$, D-Pal (1-Bu)$^6$,Lys(iPr)$^8$, D-Ala$^{10}$-LHRH.TFA | 1/8 @ 1 μg | |
| 3429 | Ac-D-Nal$^1$,4-Cl-D-Phe$^2$,D-Pal$^3$, D-Pal(Bzl)$^6$,Lys(iPr)$^8$, D-Ala$^{10}$-LHRH.TFA | 0/8 @ 1 μg 4/8 @ 0.5 μg | 6.0 |
| 3430 | Ac-D-Nal$^1$,4-Cl-D-Phe$^2$,D-Pal$^3$, Pal$^5$,D-Pal(iPr)$^6$,Lys(iPr)$^8$, D-Ala$^{10}$-LHRH.TFA | 3/8 @ 1 μg | 10 |
| 3431 | Ac-D-Nal$^1$,4-Cl-D-Phe$^2$,D-Pal$^3$, Cit$^5$,D-Cit$^6$,Lys(iPr)$^8$, D-Ala$^{10}$-LHRH.TFA | 6/8 @ 1 μg | |
| 3432 | Ac-D-Nal$^1$,4-Cl-D-Phe$^2$,D-Pal$^3$, Pal$^5$,D-Cit$^6$,Lys(iPr)$^8$, D-Ala$^{10}$-LHRH.TFA | 7/8 @ 1 μg | |
| 3433 | Ac-D-Nal$^1$,4-Cl-D-Phe$^2$,D-Pal$^3$, Cit$^5$,D-Pal$^6$,Lys(iPr)$^8$, D-Ala$^{10}$-LHRH.TFA | 5/8 @ 1 μg | |
| 3434 | Ac-D-Nal$^1$,4-Cl-D-Phe$^2$,D-Pal$^3$, Asn$^4$,Tyr$^5$,D-Cit$^6$,Lys(iPr)$^8$, D-Ala$^{10}$-LHRH.TFA | 4/8 @ 1 μg | |
| 3435 | Ac-D-Nal$^1$,4-Cl-D-Phe$^3$,D-Pal$^3$, Cit$^5$,D-Pal(iPr)$^6$,Lys(iPr)$^8$, D-Ala$^{10}$-LHRH.TFA | 7/8 @ 1 μg | |
| 3436 | Ac-D-Nal$^1$,4-Cl-D-Phe$^2$,D-Pal$^3$, D-HomoArg(NO$_2$)$^6$,Lys(iPr)$^8$, D-Ala$^{10}$-LHRH.TFA | 7/8 @ 1 μg | |
| 3437 | Ac-D-Nal$^1$,4-Cl-D-Phe$^2$,D-Pal$^3$, D-Lys(Glycolyl)$^6$,Lys(iPr)$^8$, D-Ala$^{10}$-LHRH.TFA | 7/8 @ 1 μg | |
| 3438 | Ac-D-Nal$^1$,4-Cl-D-Phe$^2$,D-Pal$^3$, D-Lys(iPrPic)$^6$,Lys(iPr)$^8$, D-Ala$^{10}$-LHRH.TFA | 2/8 @ 1 μg | 5.6 |
| 3439 | Ac-D-Nal$^1$,4-Cl-D-Phe$^2$,D-Pal$^3$, D-Lys(HomoPro)$^6$,Lys(iPr)$^8$, D-Ala$^{10}$-LHRH.TFA | 2/8 @ 1 μg | |
| 2958 | Ac-D-Nal$^1$,4-Cl-D-Phe$^2$,D-Pal$^3$, D-Pal(iPr)$^6$,Lys(iPr)$^8$, D-Ala$^{10}$-LHRH.TFA | | |
| 3440 | Ac-D-Nal$^1$,4-Cl-D-Phe$^2$,D-Pal$^3$, D-Lys(3-pyridineacetic)$^6$,Lys(iPr)$^8$, D-Ala$^{10}$-LHRH.TFA | 2/8 @ 1 μg | |
| 3441 | Ac-D-Nal$^1$,4-Cl-D-Phe$^2$,D-Pal$^3$, D-Lys(2-ClNic)$^6$,Lys(iPr)$^8$, D-Ala$^{10}$-LHRH.TFA | 8/8 @ 1 μg | |
| 3442 | Ac-N$^\alpha$Me-D-Nal$^1$,4-Cl-D-Phe$^2$, D-Pal$^3$,D-Cit$^6$,Lys(iPr)$^8$, D-Ala$^{10}$-LHRH.TFA | 7/8 @ 1 μg | |
| 3502 | Ac-D-Nal$^1$,4-Cl-D-Phe$^2$,D-Pal$^3$, Lys(Otac)$^5$,D-Lys(Otac)$^6$,Lys(iPr)$^8$, D-Ala$^{10}$-LHRH.TFA | 6/8 @ 1 μg | |
| 3503 | Ac-D-Nal$^1$,4-Cl-D-Phe$^2$,D-Pal$^3$, Lys(ONic)$^5$,D-Lys(ONic)$^6$,Lys(iPr)$^8$, D-Ala$^{10}$-LHRH.TFA | 6/8 @ 1 μg | |
| 3504 | Ac-D-Nal$^1$,4-Cl-D-Phe$^2$,D-Pal$^3$, Lys(Pyz)$^5$,D-Lys(Pyz)$^6$,Lys(iPr)$^8$, D-Ala$^{10}$-LHRH.TFA | 4/8 @ 1 μg | |
| 3552 | Ac-D-Nal$^1$,4-Cl-D-Phe$^2$,D-Pal$^3$, D-Glu$^6$,Lys(iPr)$^8$, D-Ala$^{10}$-LHRH.TFA | 8/8 @ 1 μg | |
| 3505 | Ac-D-Nal$^1$,4-Cl-D-Phe$^2$,D-Pal$^3$, D-Lys$^6$,Lys(iPr)$^8$, D-Ala$^{10}$-LHRH.TFA | 5/8 @ 1 μg | |
| 3506 | Ac-D-Nal$^1$,4-Cl-D-Phe$^2$,D-Pal$^3$, D-Lys(Gulonyl)$^6$,Lys(iPr)$^8$, D-Ala$^{10}$-LHRH.TFA | 4/8 @ 1 μg | |
| 3553 | Ac-D-Nal$^1$,4-Cl-D-Phe$^2$,D-Pal$^3$, D-Lys(iPrNic)$^5$,D-Lys(iPrNic)$^6$, Lys(iPr)$^8$,D-Ala$^{10}$-LHRH.TFA | 8/8 @ 1 μg | |
| 3507 | Ac-D-Nal$^1$,4-Cl-D-Phe$^2$,D-Pal$^3$, D-Lys(ONic)$^6$,Lys(iPr)$^8$, D-Ala$^{10}$-LHRH.TFA | 1/8 @ 1 μg | |
| 3508 | Ac-D-Nal$^1$,4-Cl-D-Phe$^2$,D-Pal$^3$, D-Lys(OTac)$^6$,Lys(iPr)$^8$, D-Ala$^{10}$-LHRH.TFA | 0/8 @ 1 μg 6/8 @ 0.5 μg | |
| 3509 | Ac-D-Nal$^1$,4-Cl-D-Phe$^2$,D-Pal$^3$, D-Lys(Pyz)$^6$,Lys(iPr)$^8$, D-Ala$^{10}$-LHRH.TFA | | |
| 3510 | Ac-D-Nal$^1$,4-Cl-D-Phe$^2$,D-Pal$^3$, D-Lys(nBuNic)$^6$,Lys(iPr)$^8$, D-Ala$^{10}$-LHRH.TFA | | |
| 3511 | Ac-D-Nal$^1$,4-Cl-D-Phe$^2$,D-Pal$^3$, D-Glu(Amp)$^6$,Lys(iPr)$^8$, D-Ala$^{10}$-LHRH.TFA | 7/8 @ 1 μg | |
| 3543 | Ac-D-Nal$^1$,4-Cl-D-Phe$^2$,D-Pal$^3$, D-Glu(Dea)$^6$,Lys(iPr)$^8$, D-Ala$^{10}$-LHRH.TFA | 6/8 @ 1 μg | |
| 3563 | Ac-D-Nal$^1$,4-Cl-D-Phe$^2$,D-Pal$^3$, Lys(pGlu)$^5$,D-Lys(pGlu)$^6$, Lys(iPr)$^8$,D-Ala$^{10}$-LHRH.TFA | | |
| 3540 | Ac-D-Nal$^1$,4-Cl-D-Phe$^2$,D-Pal$^3$, N$^\alpha$Me-Tyr$^5$,D-Pal(iPr)$^6$, Lys(iPr)$^8$,D-Ala$^{10}$-LHRH.TFA | | |
| 3541 | Ac-D-Nal$^1$,C$^\alpha$Me-4-Cl-Phe$^2$, D-Pal$^3$,N$^{\alpha Me-Tyr5}$,D-Pal(iPr)$^6$, Lys(iPr)$^8$,D-Ala$^{10}$-LHRH.TFA | 1/8 @ 1 μg | |
| 3554 | Ac-D-Nal$^1$,4-Cl-D-Phe$^2$,D-Pal$^3$, Lys(CNa)$^6$,Lys(iPr)$^8$, D-Ala$^{10}$-LHRH.TFA | | |
| 3542 | Ac-D-Nal$^1$,4-Cl-D-Phe$^2$,D-Pal$^3$, D-Glu(PEG)$^6$,Lys(iPr)$^8$, D-Ala$^{10}$-LHRH.TFA | 7/8 @ 2 μg | |
| 3565 | Ac-D-Nal$^1$,4-Cl-D-Phe$^2$,D-Pal$^3$, D-Lys(Oxa)$^6$,Lys(iPr)$^8$, D-Ala$^{10}$-LHRH.2TFA | | |
| 3551 | Ac-D-Nal$^1$,4-Cl-D-Phe$^2$,D-Pal$^3$, Lys(CNa)$^5$,D-Lys(CNa)$^6$,Lys(iPr)$^8$, D-Ala$^{10}$-LHRH.TFA | 6/8 @ 1 μg | |
| 3544 | Ac-D-Nal$^1$,4-Cl-D-Phe$^2$,D-Pal$^3$, Lys(ClNic)$^5$,D-Lys(ClNic)$^6$, Lys(iPr)$^8$,D-Ala$^{10}$-LHRH.2TFA | 6/8 @ 1 μg | |
| 3555A | Ac-D-Nal$^1$,4-Cl-D-Phe$^2$,D-Pal$^3$, D-Lys(Ac)$^6$,Lys(iPr)$^8$, D-Ala$^{10}$-LHRH.2TFA | | |
| 3564 | Ac-D-Nal$^1$,4-Cl-D-Phe$^2$,D-Pal$^3$, D-Glu(Tris)$^6$,Lys(iPr)$^8$, D-Ala$^{10}$-LHRH.2TFA | | |
| 3545 | Ac-D-Nal$^1$,4-Cl-D-Phe$^2$,D-Pal$^3$, D-Gln(iPr)$^6$,Lys(iPr)$^8$, D-Ala$^{10}$-LHRH.2TFA | 7/8 @ 1 μg | |
| 3550 | Ac-D-Nal$^1$,4-Cl-D-Phe$^2$,D-Pal$^3$, D-Glu(CSer)$^6$,Lys(iPr)$^8$, D-Ala$^{10}$-LHRH.2TFA | 6/8 @ 1 μg | |
| 3549 | Ac-D-Nal$^1$,4-Cl-D-Phe$^2$,D-Pal$^3$, D-Glu(Mop)$^6$,Lys(iPr)$^8$, D-Ala$^{10}$-LHRH.2TFA | 6/8 @ 1 μg | |
| 3548 | Ac-D-Nal$^1$,4-Cl-D-Phe$^2$,D-Pal$^3$, Lys$^5$,D-Pal(iPr)$^6$,Lys(iPr)$^8$, D-Ala$^{10}$-LHRH.4TFA | 6/8 @ 1 μg | |
| 3566 | Ac-D-Nal$^1$,4-Cl-D-Phe$^2$,D-Pal$^3$, Lys(Nic)$^5$,D-Pal(iPr)$^6$,Lys(iPr)$^8$, D-Ala$^{10}$-LHRH.3TFA | | |
| 3567 | Ac-D-Nal$^1$,4-Cl-D-Phe$^2$,D-Pal$^3$, Lys(Ac)$^5$,D-Pal(iPr)$^6$,Lys(iPr)$^8$, D-Ala$^{10}$-LHRH.3TFA | | |
| 3568 | Ac-D-Nal$^1$,4-Cl-D-Phe$^2$,D-Pal$^3$, D-Glu(DEGA)$^6$,Lys(iPr)$^8$,D-Ala$^{10}$- LHRH.2TFA | | |
| 3547 | Ac-D-Nal$^1$,4-Cl-D-Phe$^2$,D-Pal$^3$, Lys(Nic)$^5$,D-Pal(Bzl)$^6$,Lys(iPr)$^8$, D-Ala$^{10}$-LHRH.3TFA | 6/8 @ 1 μg | |
| 3569 | Ac-D-Nal$^1$,4-Cl-D-Phe$^2$,D-Pal$^3$, Lys(Ac)$^5$,D-Pal(Bzl)$^6$,Lys(iPr)$^8$, | | |

TABLE 1-continued

LHRH Antagonists

| Compound | Sequence | AO activity (AOA) | Histamine release |
|---|---|---|---|
| 3546 | Ac-D-Nal[1],4-Cl-D-Phe[2],D-Pal[3],Lys(TFAc)[6],Lys(iPr)[8],D-Ala[10]-LHRH.2TFA | 6/8 @ 1 μg | |
| 3570 | Ac-D-Nal[1],4-Cl-D-Phe[2],D-Pal[3],Lys[5],D-Pal(Bzl)[6],Lys(iPr)[8],D-Ala[10]-LHRH.3TFA | | |
| 3571 | Ac-D-Nal[1],4-Cl-D-Phe[2],D-Pal[3],Lys(iPr)[5],D-Lys(Nic)[6],Lys(iPr)[8],D-Ala[10]-LHRH.3TFA | | |
| 3572 | Ac-D-Nal[1],4-Cl-D-Phe[2],D-Pal[3],Lys(iPr)[5],D-Lys(Pic)[6],Lys(iPr)[8],D-Ala[10]-LHRH.3TFA | | |
| | Ac-D-Nal[1],4-Cl-D-Phe[2],D-Pal[3],Lys(TFAc)[5],D-Lys(TFAc)[6],Lys(iPr)[8],D-Ala[10]-LHRH.2TFA | | |
| | Ac-D-Nal[1],4-Cl-D-Phe[2],D-Pal[3],Lys(iPr)[5],4-Cl-D-Phe[6],Lys(iPr)[8],D-Ala[10]-LHRH.3TFA | | |
| | Ac-D-Nal[1],4-Cl-D-Phe[2],D-Pal[3],Lys(iPr)[5],D-Nal[6],Lys(iPr)[8],D-Ala[10]-LHRH.3TFA | | |
| | Ac-D-Nal[1],4-Cl-D-Phe[2],D-Pal[3],Lys(iPr)[5],D-Lys(pGlu)[6],Lys(iPr)[8],D-Ala[10]-LHRH.3TFA | | |
| | Ac-D-Nal[1],4-Cl-D-Phe[2],D-Pal[3],Lys(iPr)[5],D-Lys(OTac)[6],Lys(iPr)[8],D-Ala[10]-LHRH.3TFA | | |
| | Ac-D-Nal[1],4-Cl-D-Phe[2],D-Pal[3],Ile[5],D-Pal(Bzl)[6],Lys(iPr)[8],D-Ala[10]-LHRH.3TFA | | |
| | Ac-D-Nal[1],4-Cl-D-Phe[2],D-Pal[3],Lys(Pic)[5],D-Pal(iPr)[6],Lys(iPr)[8],D-Ala[10]-LHRH.3TFA | | |
| 3721 | Ac-D-Nal[1],4-Cl-D-Phe[2],D-Pal[3],D-Lys(3-Δ-Pro)[6],Lys(iPr)[8],D-Ala[10]-LHRH-TFA | 4/8 @ 1.0 | |
| 3722 | Ac-D-Nal-4-Cl-D-Phe[2],D-Pal[3],D-Lys(Ac-D-Nal[1],4-Cl-D-Phe[2],D-Pal[3],Ser)[6],Lys(iPr)[8],D-Ala[10]-LHRH.TFA | 8/8 @ 5.0 | |
| 3723 | Ac-D-Qal[1],4-Cl-D-Phe[2],D-Pal[3],D-Lys(pGlu)[6],Lys(iPr)[8],D-Ala[10]-LHRH.TFA | 7/8 @ 1.0 | |
| 3740 | Ac-D-Qal[1],4-Cl-D-Phe[2],D-Pal[3],D-Lys(Ac)[6],Lys(iPr)[8],D-Ala[10]-LHRH.TFA | 6/8 @ 1.0 | |
| 3741 | Ac-D-Nal[1],4-Cl-D-Phe[2],D-Pal[3],D-Lys(Imdac)[6],Lys(iPr)[8],D-Ala[10]-LHRH.TFA. | 1/8 @ 1.0 6/8 @ 0.5 | |
| 3742 | Ac-D-Qal[1],4-Cl-D-Phe[2],D-Pal[3],D-Lys(Dodac)[6],Lys(iPr)[8],D-Ala[10]-LHRH.TFA. | 6/8 @ 1.0 | |
| 3743 | Ac-D-Nal[1],4-Cl-D-Phe[2],D-Pal[3],Ser[5],D-Pal(iPr)[6],Lys(iPr)[8],D-Ala[10]-LHRH.2TFA | 8/8 @ 1.0 | |
| 3753 | Ac-D-Nal[1],4-Cl-D-Phe[2],D-Pal[3],D-Lys(iPr)[5],D-Lys(TFAc)[6],Lys(iPr)[8],D-Ala[10]-LHRH.2TFA | 7/8 @ 1.0 | |
| 3754 | Ac-D-Nal[1],4-Cl-D-Phe[2],D-Pal[3],His[5]D-Pal(iPr)[6],Lys(iPr)[8],D-Ala[10]-LHRH.2TFA | 5/8 @ 1.0 | |
| 3744 | Ac-D-Nal[1],4-Cl-D-Phe[2],D-Pal[3],Asn[5],D-Pal(iPr)[6],Lys(iPr)[8],D-Ala[10]-LHRH.2TFA | 7/8 @ 1.0 | |
| 3745 | Ac-D-Nal[1],4-Cl-D-Phe[2],D-Pal[3],Lys(iPr)[5],D-Lys(4HBc)[6],Lys(iPr)[8],D-Ala[10]-LHRH.2TFA | 6/8 @ 1.0 | |
| 3755 | Ac-D-Nal[1],4-Cl-D-Phe[2],D-Pal[3],Met[5],D-Pal(iPr)[6],Lys(iPr)[8],D-Ala[10]-LHRH.2TFA | 7/8 21.0 | |
| 3756 | Ac-D-Nal[1],4-Cl-D-Phe[2],D-Phe[2],D-Pal[3],Ala[5],D-Pal(iPr)[6],Lys(iPr)[8],D-Ala[10]-LHRH.2TFA | 6/8 @ 1.0 | |
| 3757 | Ac-D-Nal[1],4-Cl-D-Phe[2],D-Pal[3],N-Me-Ala[5],D-Pal(iPr)[6],Lys(iPr)[8],D-Ala[10]-LHRH.2TFA | 7/8 @ 1.0 | |
| 3758 | Ac-D-Nal[1],4-Cl-D-Phe[2],D-Pal[3],D-Lys(Hippic)[6],Lys(iPr)[8],D-Ala[10]-LHRH.TFA | 5/8 @ 1.0 | |
| 3759 | Ac-D-Nal[1],4-Cl-D-Phe[2],D-Pal[3],D-Lys(AcGly)[6],Lys(iPr)[8],D-Ala[10]-LHRH.TFA | 5/8 @ 1.0 | |
| 3760 | Ac-D-Nal[1],4-Cl-D-Phe[2],D-Pal[3],D-Lys(Ppic)[6],Lys(iPr)[8],D-Ala[10]-LHRH.TFA | 1/8 @ 1.0 7/8 @ 0.5 | |
| 3761 | Ac-D-Nal[1],4-Cl-D-Phe[2],D-Pal[3],D-Lys(Mts)[6],Lys(iPr)[8],D-Ala[10]-LHRH.TFA | 7/8 @ 1.0 | |
| 3762 | Ac-D-Nal[1],4-Cl-D-Phe[2],D-Pal[3],D-Lys(Orotic)[6],Lys(iPr)[8],D-Ala[10]-LHRH.TFA | 6/8 @ 1.0 | |
| 3763 | Ac-Sar[1],4-Cl-D-Phe[2],D-Nal[3],D-Pal(Bzl)[6],Lys(iPr)[8],D-Ala[10]-LHRH.2TFA | 4/8 @ 1.0 | 102[1],76[b] |
| 3769 | Ac-Sar[1],4-Cl-D-Phe[2],1-1-Nal[3],D-Pal(Bzl)[6],Lys(iPr)[8],D-Ala[10]-LHRH.2TFA | 6/8 @ 1.0 | |
| 3770 | Ac-D-Nal[1],4-Cl-D-Phe[2],D-Pal[3],D-Pal(CH$_2$COOH)[6],Lys(iPr)[8],D-Ala[10]-LHRH.TFA | 6/8 @ 1.0 0.1 DMSO | |
| 3771 | Ac-D-Nal[1],4-Cl-D-Phe[2],D-Pal[3],D-Lys(Ala)[6],Lys(iPr)[8],D-Ala[10]-LHRH.TFA | 7/8 @ 1.0 | |
| 3772 | Ac-Sar[1],4-Cl-D-Phe[2],D-1-Nal[3],D-Pal(iPr)[6],Lys(iPr)[8],D-Ala[10]-LHRH.2TFA | 8/8 @ 1.0 | |
| 3773 | Ac-Sar[1],4-Cl-D-Phe[2],L-1-Nal[3],D-Pal(iPr)[6],Lys(iPr)[8],D-Ala[10]-LHRH.2TFA | 7/8 @ 1.0 | |
| 3785 | Ac-D-Qal[1],4-Cl-D-Phe[2],D-Pal[3],D-Lys(Gulonyl)[6],Lys(iPr)[8],D-Ala[10]-LHRH.TFA | 7/8 @ 1.0 0.1 DMSO | |
| 3786 | Ac-D-Nal[1],4-Cl-D-Phe[2],D-Pal[3],D-Pal(N-O)[6],Lys(iPr)[8],D-Ala[10]-LHRH.TFA | 4/8 @ 1.0 | |
| 3787 | Ac-D-Qal[1],4-Cl-D-Phe[2],D-Pal[3],D-Lys(Ppic)[6],Lys(iPr)[8],D-Ala[10]-LHRH.TFA | 7/8 @ 1.0 | |
| 3800 | Ac-D-Qal[1],4-Cl-D-Phe[2],D-Pal[3],D-Lys(Imdac)[6],Lys(iPr)[8],D-Ala[10]-LHRH.TFA | 7/8 @ 1.0 | |
| 3801 | Ac-D-Qal[1],4-Cl-D-Phe[2],D-Pal[3],D-Lys(Onic)[6],Lys(iPr)[8],D-Ala[10]-LHRH.TFA | 8/8 @ 1.0 | |
| 3802 | Ac-D-Qal[1],4-Cl-D-Phe[2],D-Pal[3],D-Lys(Otac)[6],Lys(iPr)[8],D-Ala[10]-LHRH.TFA | 5/8 @ 1.0 | |
| 3803 | Ac-D-Nal[1],4-Cl-D-Phe[2],D-Pal[3],D-Lys(Dodac)[6],Lys(iPr)[8],D-Ala[10]-LHRH.TFA | 2/8 @ 1.0 | |
| 3804 | Ac-D-Pal[1],4-Cl-D-Phe[2],D-Pal[3],D-Pal(iPr)[6],Lys(iPr)[8],D-Ala[10]-LHRH.2TFA | 8/8 @ 1.0 | 8/8 @ 1.0 |
| 3827 | Ac-D-Nal[1],4-Cl-D-Phe[2],D-Pal[3],N-Me-Tyr[5],D-Asn[6],Lys(iPr)[8],D-Ala[10]-LHRH.TFA | 4/8 @ 1.0 | |
| 3828 | Ac-D-Nal[1],4-Cl-D-Phe[2],D-Pal[3],N-Me-Tyr[5],D-Lys(Onic)[8],Lys(iPr)[8],D-Ala[10]-LHRH.TFA | 4/8 @ 1.0 | 42[a],39[b] |
| 3829 | Ac-D-Nal[1],4-Cl-D-Phe[2],D-Pal[3],N-Me-Tyr[5],D-Lys(Ac)[6],Lys(iPr)[8],D-Ala[10]-LHRH.TFA | 8/8 @ 1.0 | |
| 3852 | Ac-D-Nal[1],4-Cl-D-Phe[2],D-Pal[3],Lys(iPr)[5],D-His[6],Trp[7],Orn[8],D-Ala[10]-LHRH.TFA | 8/8 @ 5.0 | |
| 3853 | Ac-D-Nal[1],4-Cl-D-Phe[2],D-Pal[3],His[5],D-Arg[6],Trp[7],Orn[8], | 0/8 @ 5.0 | |

TABLE 1-continued

LHRH Antagonists

| Compound | Sequence | AO activity (AOA) | Histamine release |
|---|---|---|---|
| 3854 | Ac-D-Nal$^1$,4-Cl-D-Phe$^2$,D-Pal$^3$,Arg$^5$, D-His$^6$,Trp$^7$,Orn$^8$, D-Ala$^{10}$-LHRH.TFA | 6/8 @ 5.0 | |
| 3855 | Ac-D-Nal$^1$,4-Cl-D-Phe$^2$,D-Pal$^3$, Lys(iPr)$^5$,D-Trp$^6$,Trp$^7$,Orn$^8$, D-Ala$^{10}$-LHRH.TFA | 4/8 @ 1.0 | |
| 3851 | Ac-D-Nal$^1$,4-Cl-D-Phe$^2$,D-Pal$^3$, 4-Cl-Phe$^5$,D-Pal(iPr)$^6$,Lys(iPr)$^8$, D-Ala$^{10}$-LHRH.2JFA | 0/8 @ 1.0 6/8 @ 0.5 | 4.1$^a$,5.4$^b$ |
| 3882 | Ac-D-Nal$^1$,4-Cl-D-Phe$^2$, D-Pal(N-O)$^3$,D-Pal(iPr)$^6$, Lys(iPr)$^8$,D-Ala$^{10}$-LHRH.2JFA | 6/8 @ 1.0 | |
| 3880 | Ac-D-Nal$^1$,4-Cl-D-Phe$^2$,D-Trp$^3$, Met$^8$,D-Ala$^{10}$-LHRH.TFA | 8/8 @ 1.0 | |
| 3878 | Ac-D-Nal$^1$,4-Cl-D-Phe$^2$,D-Trp$^3$, D-Arg$^6$,Met(S $^+$ Me)$^8$, D-Ala$^{10}$-LHRH.2TFA | 2.8 @ 1.0 7/8 @ 0.5 | |
| 3881 | Ac-D-Nal$^1$,4-Cl-D-Phe$^2$,D-Trp$^3$, D-Met$^6$,D-Ala$^{10}$-LHRH.TFA | 7/8 @ 1.0 | |
| 3879 | Ac-D-Nal$^1$,4-Cl-D-Phe$^2$,D-Trp$^3$, Met(S $^+$ Me)$^6$, D-Ala$^{10}$-LHRH.2TFA | 0/8 @ 1.0 6/8 @ 0.5 | |
| 3926 | Ac-D-Nal$^1$,4-Cl-D-Phe$^2$,D-Trp$^3$, D-Arg$^6$,Lys(COCH$_2$Br)$^8$, D-Ala$^{10}$-LHRH.TFA | 6/8 @ 1.0 | |
| 3925 | Ac-D-Nal$^1$,4-Cl-D-Phe$^2$,D-Trp$^3$, D-Met(S $^+$ Me)$^6$,Met(S $^+$ Me)$^8$, D-Ala$^{10}$-LHRH.2TFA | 5/8 @ 1.0 | 13$^c$,5$^d$ |
| 3941 | Met(S $^+$ Me)$^8$-LHRH.TFA | 8/8 @ 50.0 | |
| 3942 | Lys(COCH$_2$Br)$^8$-LHRH | 8/8 @ 50.0 | |
| 3948 | Ac-D-Nal$^1$,4-Cl-D-Phe$^2$,D-Trp$^3$, D-Lys(COCH$_2$Br)$^6$, D-Ala$^{10}$-LHRH.TFA | low activity | |
| 3949* | Ac-D-Nal$^1$,4-Cl-D-Phe$^2$,D-Pal$^3$, D-Lys(COCH$_2$CH$_2$N(Et)$_2$)$^6$, D-Ala$^{10}$-LHRH.2TFA | low activity | |
| 3960 | Ac-D-Nal$^1$,4-Cl-D-Phe$^2$,D-Pal$^3$, D-Lys(2-pyrimidylthio)$^6$, Lys(iPr)$^8$,D-Ala -LHRH.TFA | 5/8 @ 1.00 | |
| 3961 | Ac-D-Nal$^1$,4-Cl-D-Phe$^2$,D-Trp$^3$, Met(S $^+$ CH$_2$C$_6$H$_5$)$^6$, D-Ala$^{10}$-LHRH.2TFA | 4/8 @ 2.00 3/8 @ 1.00 | |
| 3967 | Ac-D-Nal$^1$,4-Cl-D-Phe$^2$,D-Pal$^3$, D-Met(S $^+$ CH$_3$)$^6$, D-Ala$^{10}$-LHRH.2TFA | 1/8 @ 0.5 7/8 @ 0.25 | 0.3$^e$,0.15$^f$ |
| 3968* | Ac-D-Nal$^1$,4-Cl-D-Phe$^2$,D-Pal$^3$, D-Met(S $^+$ CH$_2$COPh)$^6$, D-Ala$^{10}$-LHRH.2TFA | 4/8 @ 1.00 | |
| 3969 | Ac-D-Nal$^1$,4-Cl-D-Phe$^2$,D-Pal$^3$, Dap(COCH$_2$S + Me$_2$)$^6$, D-Ala$^{10}$-LHRH.2TFA | 3/8 @ 1.00 | |
| 3982 | Ac-D-Nal$^1$,4-Cl-D-Phe$^2$,D-Pal$^3$, His$^5$D-Pal(iPr)$^6$,Lys(iPr)$^8$, D-Ala$^{10}$-LHRH.2TFA | 8/8 @ 1.00 | 53$^c$,33$^d$ |
| 3983 | Ac-D-Nal$^1$,4-Cl-D-Phe$^2$,D-Pal$^3$, D-Arg$^6$,Met(S + Me)$^8$, D-Ala$^{10}$-LHRH.2TFA | 0/8 @ 1.00 8/8 @ 0.5 | 5.35$^g$,1.32 h |
| 3984 | Ac-D-Nal$^1$,4-Cl-D-Phe$^2$,D-Trp$^3$, D-Met(S + CH$_2$ – CH = CH$_2$)$^6$, D-Ala$^{10}$-LHRH.2TFA | 3/8 @ 1.00 | |
| 3985 | Ac-D-Nal$^1$,4-Cl-D-Phe$^2$,D-Pal$^3$, D-Arg$^6$,Orn(COCH$_2$S + Me$_2$)$^8$, D-Ala$^{10}$,LHRH.2TFA | 0/8 @ 1.00 8/8 @ 0.5 | 4.4$^a$,3.86$^b$ |
| 3994 | Ac-D-Nal$^1$,4-Cl-D-Phe$^2$,D-Pal$^3$, D-Arg$^6$,Orn(COCH$_2$SMe)$^8$, D-Ala$^{10}$-LHRH.2TFA | 6/8 @ 1.00 | |
| 3995 | Ac-D-Nal$^1$,4-Cl-D-Phe$^2$,D-Pal$^3$, D-Arg$^6$,MET$^8$,D-Ala$^{10}$-LHRH.TFA | 5/8 @ 1.00 | |
| 4014 | Ac-D-Nal$^1$,4-Cl-D-Phe$^2$,D-Pal$^3$, D-Lys(COCH$_2$S + Me$_2$)$^6$, D-Ala$^{10}$-LHRH.2TFA | 0/8 @ 1.00 | |
| 4015 | Ac-D-Nal$^1$,4-Cl-D-Phe$^2$,D-Pal$^3$, D-Arg$^6$,Lys(COCH$_2$S + Me$_2$)$^8$, D-Ala$^{10}$-LHRH.2TFA | 1/8 @ 1.00 | |
| 4016 | Ac-D-Nal$^1$,4-Cl-D-Phe$^2$,D-Pal$^3$, D-Met(S + Me)$^6$,Met(S + Me)$^8$, D-Ala$^{10}$-LHRH.2TFA | 6/8 @ 1.00 | |
| 4013 | Ac-D-Nal$^1$,4-Cl-D-Phe$^2$,D-Pal$^3$, D-Orn(COCH$_2$S + Me$_2$)$^6$, D-Ala$^{10}$-LHRH.2TFA | 0/8 @ 1.00 | |
| 4023 | Ac-D-Nal$^1$,4-Cl-D-Phe$^2$,D-Pal$^3$, D-Arg$^6$,Dap(COCH$_2$S + Me$_2$)$^8$, D-Ala$^{10}$-LHRH.2TFA | 0/8 @ 1.00 | |

* = Mass spectral analysis did not confirm the structure,
Nal arg (reference) histamine release values: a = 0.11, b = 0.14, C = 0.28, d = 0.11, e = 0.1, f = 0.02, g = 0.1, h = 0.02

Sulfonium moieties confer high AOA on peptides when incorporated at position 6 (e.g., compound 3879) or position 8 (e.g., compound 3983). Compound 3925 (with two sulfonium moieties) showed low histamine release. Both alkyl and α-(sulfonium)carbonyl moieties (e.g., compound 4023) are effective. Preliminary experiments with LHRH agonists and antagonists suggest that compounds incorporating a bromoacetyl moiety are bound to the receptor and are not removed by repeated washing.

Certain peptides which have an N-alkyl pyridinium moiety at position 6 are unexpectedly active (e.g. compound 3851) in the AOA assay. Some have very little histamine-releasing activity (e.g., compound 3763) compared to the standard, Nal-Arg. These results are unexpected in light of the previously reported AOA activity and histamine-releasing qualities of N-methyl pyridinium compounds.

Dipolar moieties generally exhibited modest AOA. Compounds including Lys(Onic)$^6$ exhibited favorable qualities; one (compound 3828) showed low histamine releasing activity, and compound 3507 showed high AOA.

Several peptides having acylated lysine at position 6 were tested, and showed good AO activity (e.g. compounds 3741 and 3760).

Compounds having a small polar moiety at position 6 exhibited favorable combinations of AOA and histamine-releasing activity. For example, compound 3827, which has D-Asn (a small, hydrophilic moiety) at position 6 showed moderate AO activity. Compounds 3341, 3342, and 3343 having D-Gln, D-Asn, and D-Thr, respectively, combined moderate AOA with very low histamine release. Compound 3361, which had the taurine amide of Glu at position 6, also showed very low histamine release. Compound 3369, which had D-Cit at position 6, also showed low histamine release.

All of the analogs listed in Table 1 can by synthesized by the solid phase method using an automated synthesizer (e.g., Beckman Model 990). The amino acid residues used can be purchased from commercial sources (e.g. Aldrich Chemical Co., Milwaukee, Wis.), or can be produced from commercially available starting materials according to known methods. For example, pyridinium-N-oxides can be produced by oxidation of the corresponding pyridine with, e.g., peroxyacids such as mCPBA (see, e.g., Example 3, infra). Pyridinium moieties, for example, N-benzyl pyridinium compounds, can be produced by N-alkylation of the corresponding pyridine, e.g., by heating in an inert solvent with benzyl bromide (see Examples 1 and 2, infra). Similarly, sulfonium and phosphonium salts can be produced by S- or P-alkylation of a sulfide or phosphine, respectively, with an alkylating agent such as, for example, methyl iodide. Amino acids which are not obtained commercially can be synthesized in a protected form for coupling, or, if appropriate, can be coupled to form a peptide and subsequently modified to the desired form.

EXAMPLE 2

Synthesis of Boc-D-Pal(Bzl) hydrobromide Salt

Boc-D-Pal (1.36 g, 6.0 mmol) was suspended in 60 ml of acetonitrile. Benzyl bromide (about 50 mmol) was added and the mixture was warmed to 50° C. on a water bath. A cleasr solution resulted, and was stirred at room temperature for 16 hours. A white precipitate formed; TLC after 17 hours showed some starting remaining starting material; stirring continued for a total of 5 days, when the reaction was complete. The solvent was evaporated under reduced pressure, and the residue recrystallized from EtOH/ethyl acetate. Yield: 85%; m.p. 166–170° C.

EXAMPLE 3

Synthesis of Boc-D-Pal(iPr)

Boc-D-Pal (4.0 g, 17.7 mmol) and $Ag_2O$ (8.0 g, 34.4 mmol) in 22 ml water was stirred at room temperature for 4 hours. The reaction vessel was cooled to 0° C., and 2-iodopropane (20.4 g, 120 mmol) in 40 ml 2-propanol was added. After addition was complete, the mixture was allowed to warm to room temperature and stirred for 4 days. Additional $Ag_2O$ (2 g) and 2-iodopropane (2 g) were added after 24 hours and again after 48 hours. The mixture was filtered, and the precipitate was washed with ethanol (2×15 ml). The filtrate was evaporated to yield 4.3 g of a yellow oil. Crystallization from ethanol/ethyl acetate gave light yellow crystals (3.0 g); Yield: 63%; m.p. 182–185° C.

EXAMPLE 4

Synthesis of Boc-D-Pal(N—O)

Boc-D-Pal (2.0 g, 7.5 mmole) was dissolved in 40 ml acetone and 2.48 g (16.5 mmol) of MCPBA (57–86%; purchased from Aldrich and used as received) in 80 ml acetone was added in one portion. The mixture was stirred at room temperature for 40 hours; a small amount of white precipitate formed as the reaction proceeded. The precipitated was filtered and the mother liquor evaporated to yield a white precipitate. The combined solids were washed with ether (to remove chlorobenzoic acid) and recrystallized from ethyl acetate/hexane. Yield: 1.7 g (80%); m.p. 155–157° C.

EXAMPLE 5

Peptide Synthesis

A typical coupling cycle for peptide synthesis with Boc-amino acids on a peptide synthesizer (Beckman Model 990) was as follows:

Methylbenzyhydramine (MBHA) resin (1.18 g, 0.85 meq amino groups/g resin) was weighed into the reaction vessel and washed with two protions of chloroform (26 ml each). The resin was prewashed with 22% thioanisole (5 ml)166% trifluoroacetic acid (TFA) in 14 ml dichloromethane (DCM) for 5 minutes, and then deprotected for 30 minutes with the same thioanisole/TFA mixture. The resin was washed with three portions of chloroform (20 ml each), two portions of 2-propanol (26 ml each) and two portions of DCM (26 ml each). The resin was neutralized with two portions of 12% diisopropylethylamine (DIPEA) (26 ml each), and then washed with four portions of DCM (26 ml each), followed by two portions of 1:1 DCM:dimethylformamide (DMF) (26 ml each). A solution of a Boc-protected amino acid (2.5 mole equivalents) and HOBt (2.5 mole equivalents) was introduced as a solution in 10 ml DMF, and DCC was added (256 mg in 6 DMF). Coupling was allowed to proceed for three hours, or overnight. Hindered residues (e.g., backbone N-methyl amino acids) required longer coupling times. The resin was washed with two 26 ml portions of DMF, followed by two 26 ml portions of 2-propanol and then two 26 ml portions of DCM. Completion of coupling was assessed by Kaiser's test (ninhydrin test). If coupling is not complete, a double coupling was performed (i.e., the resin was neutralized as above and the coupling step repeated). When complete coupling is achieved, the cycle was repeated with the next amino acid.

Upon completion of the synthesis, the peptide was cleaved from the resin by treatment with liquid hydrofluoric acid (HF) for 45 minutes at 0° C. The HF was evaporated and the the peptide treated with aqueous acetic acid and lyophilized. The crude peptide was then purified by high performance liquid chromatography (HPLC) on a $C_{18}$ column, eluting with a mixture of acetonitrile and 0.1% TFA in water. Purified fractions (homogeneous by UV and TLC analysis) were combined and lyophilized. Analytical HPLC was used to determine the purity of the final product; all peptides synthesized were at least 98% pure.

EXAMPLE 6

Suppression of Plasma Testosterone Levels

The ability of an LHRH antagonist of the invention to suppress plasma testosterone levels was examined in adult male rats. The rats were administered the LHRH antagonist #3827 (the structure of which is shown in Table 1). In one experiment, a single injection of LHRH antagonist was administered subcutaneously at doses of 300 or 1000 $\mu$g/kg. Animals showed a rapid, pronounced decrease in plasma testosterone to nearly undetectable levels by hours 6 hours post-administration. Testosterone levels returned to normal by 24 hours after the 300 $\mu$g/kg dose, but not until 72 hours after the 1000 $\mu$g/kg dose.

In another experiment, the LHRH antagonist #3827 was administered in eight intravenous doses of 1, 10 or 100 $\mu$g/kg, each every three hours, corresponding respectively to 8, 80 or 800 $\mu$g/kg/day. The results are shown graphically in FIG. 1. Castrate levels of testosterone were achieved at doses of 10 $\mu$g/kg every three hours. A dose as low as 1 $\mu$g/kg, equivalent to 8 $\mu$g/kg/day, induced a significant decrease in plasma testosterone levels throughout the experimental period.

Figure 2:
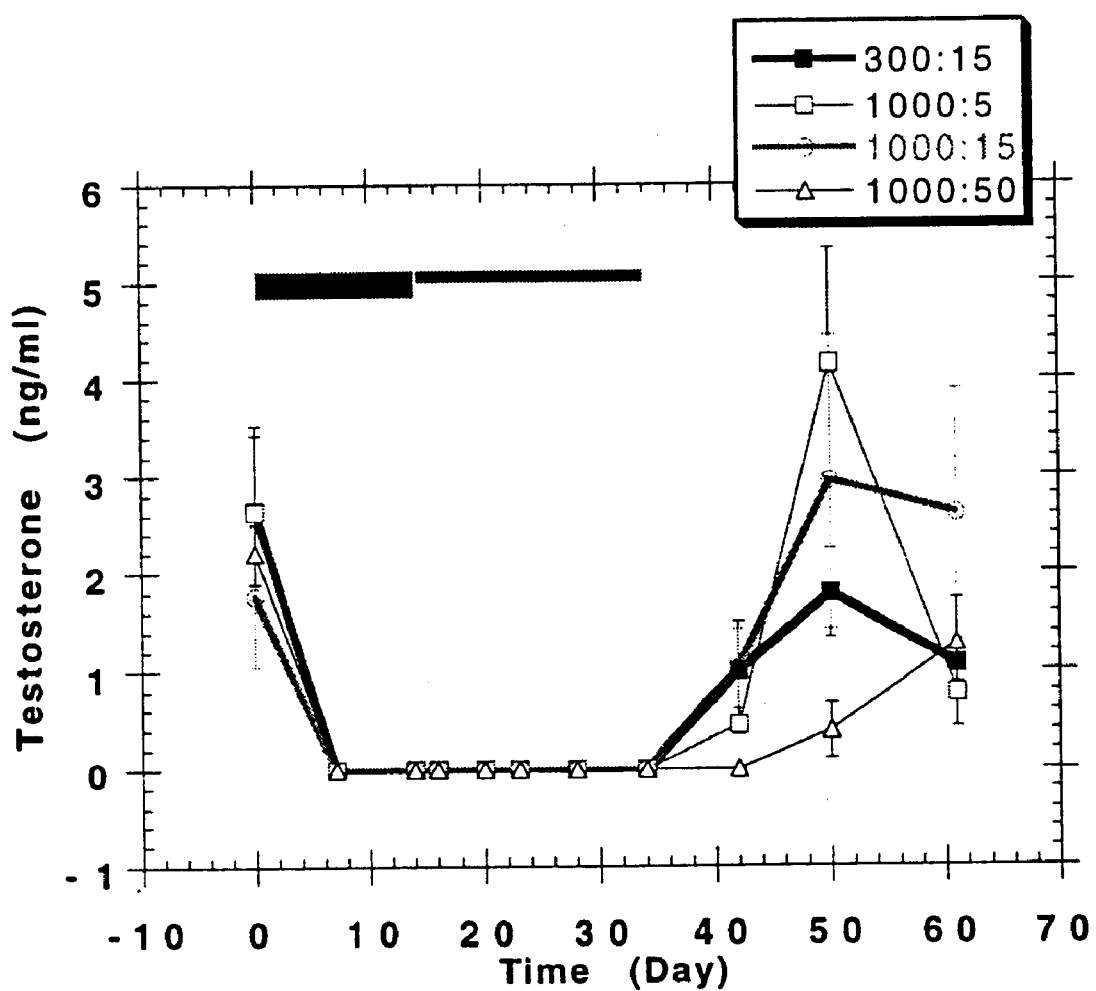
FIG. 2 is a graph depicting plasma testosterone levels (in ng/ml) in adult male rats subcutaneously administered the LHRH antagonist #3827 via an osmotic pump. Doses were either 300 µg/kg/day for two weeks, followed by 15 µg/kg/day for an additional two weeks or 1000 µg/kg/day for two weeks, followed by 5, 15 or 50 µg/kg/day for an additional two weeks.
Figure 3:
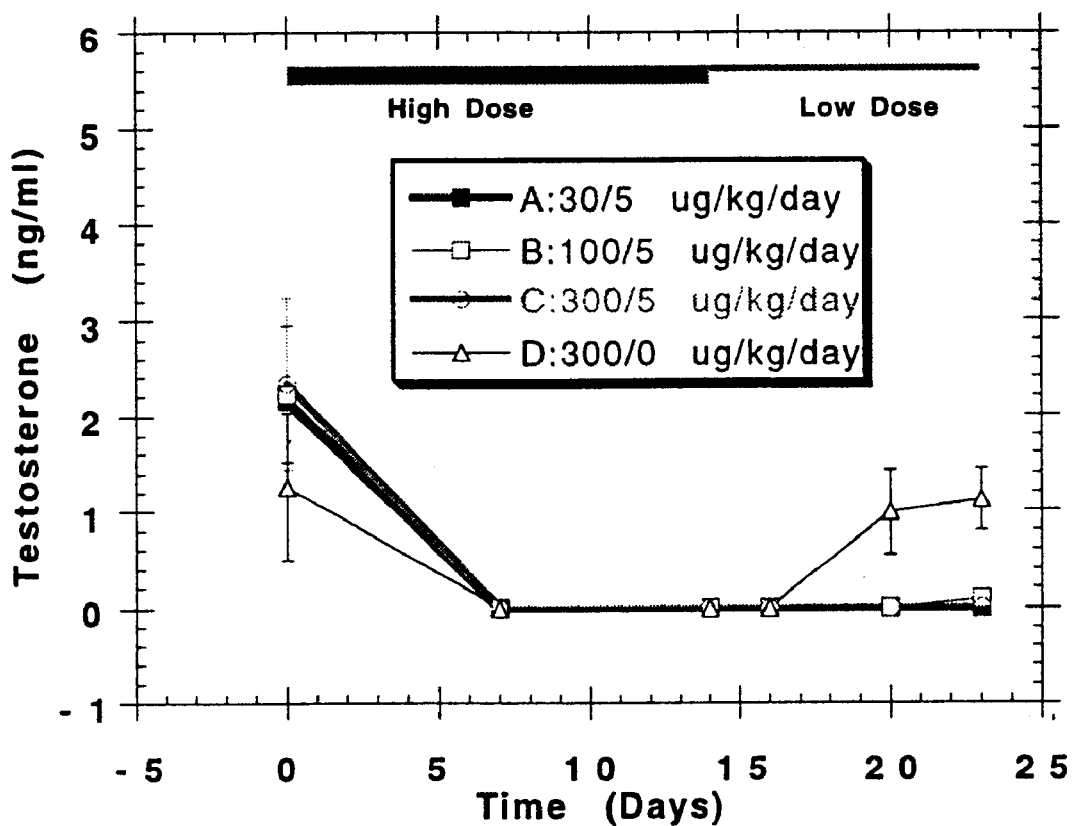
FIG. 3 is a graph depicting the plasma testosterone levels (in ng/ml) in adult male rats subcutaneously administered the LHRH antagonist #3827 via an osmotic pump. Doses were either 30 µg/kg/day for two weeks, followed by 5 µg/kg/day for an additional two weeks, 100 µg/kg/day for two weeks, followed by 5 µg/kg/day for an additional two weeks. or 300 µg/kg/day for two weeks, followed by 0 or 5 µg/kg/day for an additional two weeks.

In another experiment, continuous subcutaneous infusion of the LHRH antagonist #3827 was achieved through use of an osmotic pump. Doses of 300 or 1000 $\mu$g/kg/day ("High Dose") were administered subcutaneously for two weeks via Alzet osmotic minipumps in each of five male Sprague-Dawley rats. The animals that received 1000 $\mu$g/kg/day were then maintained for an additional two weeks with 5, 15 or 50 $\mu$g/kg/day ("Low Dose") before the pumps were removed completely. The results are shown graphically in FIG. 2. Chronic treatment of rats with the LHRH antagonist at initial doses of 300 or 1000 $\mu$g/kg/day resulted in castrate levels of testosterone within the first 7 days (and presumably within the first 24 hours) with either initial dose, and were maintained by all three subsequent doses for an additional 21 days. Castration was maintained throughout this period with no apparent "castration response" as has been described with other inhibitors. When the High Dose pumps were replaced with maintenance Low Dose pumps giving doses as low as 5 μg/kg/day, animals remained fully castrated throughout the experiment. Following completion of LHRH antagonist treatment, a dose dependent recovery in plasma testosterone was observed: animals that received the highest maintenance dose appeared to recover more slowly than animals treated with the lower maintenance doses. Recovery of testosterone levels following pump removal was complete within two weeks. In a follow up study, the results of which are shown graphically in FIG. 3, complete suppression of testosterone to castrate levels was achieved by doses as low as 30 μg/kg/day. Castrate levels were again maintained with a dose of LHRH antagonist as low as 5 μg/kg/day

EQUIVALENTS

Those skilled in the art will recognize, or be able to ascertain using no more than routine experimentation, many equivalents to the specific embodiments of the invention described herein. Such equivalents are intended to be encompassed by the following claims.

I claim:

1. A method of treating a subject having a disorder associated with LHRH activity, comprising administering to a subject an effective amount of a peptide compound which inhibits LHRH activity, wherein the peptide compound comprises a structure:

A-B-C-D-E-F-G-H-I-J wherein
A is pyro-Glu, Ac-D-Nal, Ac-D-Qal, Ac-Sar, or Ac-D-Pal;
B is His or 4-Cl-D-Phe;
C is Trp, D-Pal, D-Nal, L-Nal-D-Pal(N—O), or D-Trp;
D is Ser;
E is N-Me-Ala, Tyr, N-Me-Tyr, Ser, Lys(iPr), 4-Cl-Phe, His, Asn, Met, Ala, Arg or Ile;
F is D-Asn or D-Gln;
G is Leu or Trp;
H is Lys(iPr), Gln, Met, or Arg;
I is Pro; and
J is Gly-NH$_2$ or D-Ala-NH$_2$;
or a pharmaceutically acceptable salt thereof, thereby treating a subject having a disorder associated with LHRH activity.

2. A method of treating a subject having a disorder associated with LHRH activity, comprising administering to a subject an effective amount of a peptide compound which inhibits LHRH activity, wherein the peptide compound comprises a structure:

A-B-C-D-E-F-G-H-I-J wherein
A is pyro-Glu, Ac-D-Nal, Ac-D-Qal, Ac-Sar, or Ac-D-Pal;
B is His or 4-Cl-D-Phe;
C is Trp, D-Pal, D-Nal, L-Nal-D-Pal(N—O), or D-Trp;
D is Ser;
E is N-Me-Ala, Tyr, N-Me-Tyr, Ser, Lys(iPr), 4-Cl-Phe, His, Asn, Met, Ala, Arg or Ile;
F is D-Asn;
G is Leu or Trp;
H is Lys(iPr), Gln, Met, or Arg;
I is Pro; and
J is Gly-NH$_2$ or D-Ala-NH$_2$;
or a pharmaceutically acceptable salt thereof, thereby treating a subject having a disorder associated with LHRH activity.

3. The method of any one of claim 1 or 2, wherein said peptide compound comprises a structure:

Ac-D-Nal-4-Cl-D-Phe-D-Pal-Ser-N-Me-Tyr-D-Asn-Leu-Lys(iPr)-Pro-D-Ala-NH$_2$;

or a pharmaceutically acceptable salt thereof.

4. The method of any one of claim 1 or 2, wherein said peptide compound comprises a structure:

Ac-D-Nal-4-Cl-D-Phe-D-Pal-Ser-Tyr-D-Asn-Leu-Lys(iPr)-Pro-D-Ala-NH$_2$;

or a pharmaceutically acceptable salt thereof.

5. A method of treating a subject having a disorder associated with LHRH activity, comprising administering to a subject an effective amount of a peptide compound which inhibits LHRH activity, wherein the peptide compound comprises a structure:

A-B-C-D-E-F-G-H-I-J, wherein
A is D-Glu, L-Glu, or an analogue thereof;
B is D-His, L-His, or an analogue thereof;
C is D-Trp, L-Trp, or an analogue thereof;
D is D-Ser, L-Ser, or an analogue thereof;
E is D-Tyr, L-Tyr, or an analogue thereof;
F is D-asparagine, L-asparagine, D-glutamine, or L-glutamine;

G is D-Leu, L-Leu or an analogue thereof;

H is D-Arg, L-Arg, or an analogue thereof;

I is D-Pro, L-Pro, or an analogue thereof; and

J is D-Gly, L-Gly, or an analogue thereof; or a pharmaceutically acceptable salt thereof.

6. A method of treating a subject having a disorder associated with LHRH activity, comprising administering to a subject an effective amount of a peptide compound which inhibits LHRH activity, wherein the peptide compound comprises a structure:

A-B-C-D-E-F-G-H-I, wherein

A is D-Glu, L-Glu, or an analogue thereof;

B is D-His, L-His, or an analogue thereof;

C is D-Trp, L-Trp, or an analogue thereof;

D is D-Ser, L-Ser, or an analogue thereof;

E is D-Tyr, L-Tyr, or an analogue thereof;

F is D-asparagine, L-asparagine, D-glutamine, or L-glutamine;

G is D-Leu, L-Leu or an analogue thereof;

H is D-Arg, L-Arg, or an analogue thereof; and

I is D-Pro, L-Pro, or an analogue thereof;

or a pharmaceutically acceptable salt thereof.

7. A method of treating a subject having a disorder associated with LHRH activity, comprising administering to a subject an effective amount of a peptide compound which inhibits LHRH activity, wherein the peptide compound comprises a structure:

A-B-C-D-E-F-G-H-I-J wherein

A is pyro-Glu, Ac-Nal, Ac-Qal, Ac-Sar, or Ac-Pal, or an analogue thereof;

B is His or 4-Cl-Phe, or an analogue thereof;

C is Trp, Pal, Nal, Nal-Pal(N—O), or Trp, or an analogue thereof;

D is Ser, or an analogue thereof;

E is N-Me-Ala, Tyr, N-Me-Tyr, Ser, Lys(iPr), 4-Cl-Phe, His, Asn, Met, Ala, Arg or Ile, or an analogue thereof;

F is Asn or Gln;

G is Leu or Trp, or an analogue thereof;

H is Lys(iPr), Gln, Met, or Arg, or an analogue thereof;

I is Pro, or an analogue thereof; and

J is Gly-NH$_2$ or Ala-NH$_2$, or an analogue thereof;

or a pharmaceutically acceptable salt thereof.

8. The method of claim 7, wherein the peptide compound comprises the structure:

A-B-C-D-E-F-G-H-I-J wherein

A is pyro-Glu, Ac-Nal, Ac-Qal, Ac-Sar, or Ac-Pal, or an analogue thereof;

B is His or 4-Cl-Phe, or an analogue thereof;

C is Trp, Pal, Nal, L-Nal-Pal(N—O), or Trp, or an analogue thereof;

D is Ser, or an analogue thereof;

E is N-Me-Ala, Tyr, N-Me-Tyr, Ser, Lys(iPr), 4-Cl-Phe, His, Asn, Met, Ala, Arg or Ile, or an analogue thereof;

F is Asn;

G is Leu or Trp, or an analogue thereof;

H is Lys(iPr), Gln, Met, or Arg, or an analogue thereof;

I is Pro, or an analogue thereof; and

J is Gly-NH$_2$ or Ala-NH$_2$, or an analogue thereof;

or a pharmaceutically acceptable salt thereof.

9. A method of treating a subject having a disorder associated with LHRH activity, comprising administering to a subject an effective amount of a peptide compound which inhibits LHRH activity, wherein the peptide compound comprises a structure:

A-B-C-D-E-F-G-H-I wherein

A is pyro-Glu, Ac-Nal, Ac-Qal, Ac-Sar, or Ac-Pal, or an analogue thereof;

B is His or 4-Cl-Phe, or an analogue thereof;

C is Trp, Pal, Nal, Nal-Pal(N—O), or Trp, or an analogue thereof;

D is Ser, or an analogue thereof;

E is N-Me-Ala, Tyr, N-Me-Tyr, Ser, Lys(iPr), 4-Cl-Phe, His, Asn, Met, Ala, Arg or Ile, or an analogue thereof;

F is Asn or Gln;

G is Leu or Trp, or an analogue thereof;

H is Lys(iPr), Gln, Met, or Arg, or an analogue thereof; and

I is Pro, or an analogue thereof;

or a pharmaceutically acceptable salt thereof.

10. The method of claim 9, wherein the peptide compound comprises the structure:

A-B-C-D-E-F-G-H-I wherein

A is pyro-Glu, Ac-Nal, Ac-Qal, Ac-Sar, or Ac-Pal, or an analogue thereof;

B is His or 4-Cl-Phe, or an analogue thereof;

C is Trp, Pal, Nal, L-Nal-Pal(N—O), or Trp, or an analogue thereof;

D is Ser, or an analogue thereof;

E is N-Me-Ala, Tyr, N-Me-Tyr, Ser, Lys(iPr), 4-Cl-Phe, His, Asn, Met, Ala, Arg or Ile, or an analogue thereof;

F is Asn;

G is Leu or Trp, or an analogue thereof;

H is Lys(iPr), Gln, Met, or Arg, or an analogue thereof; and

I is Pro, or an analogue thereof;

or a pharmaceutically acceptable salt thereof.

11. A method of treating a subject having a disorder associated with LHRH activity, comprising administering to a subject an effective amount of a peptide compound which inhibits LHRH activity, wherein the peptide compound comprises a structure:

A-B-C-D-E-F-G-H-I wherein

A is pyro-Glu, Ac-D-Nal, Ac-D-Qal, Ac-Sar, or Ac-D-Pal, or an analogue thereof;

B is His or 4-Cl-D-Phe, or an analogue thereof;

C is Trp, D-Pal, D-Nal, L-Nal-D-Pal(N—O), or D-Trp, or an analogue thereof;

D is Ser, or an analogue thereof;

E is N-Me-Ala, Tyr, N-Me-Tyr, Ser, Lys(iPr), 4-Cl-Phe, His, Asn, Met, Ala, Arg or Ile, or an analogue thereof;

F is D-Asn or D-Gln;

G is Leu or Trp, or an analogue thereof;

H is Lys(iPr), Gln, Met, or Arg, or an analogue thereof; and

I is Pro, or an analogue thereof;

or a pharmaceutically acceptable salt thereof.

12. The method of claim 11, wherein the peptide compound comprises the structure:

A-B-C-D-E-F-G-H-I wherein

A is pyro-Glu, Ac-D-Nal, Ac-D-Qal, Ac-Sar, or Ac-D-Pal, or an analogue thereof;

B is His or 4-Cl-D-Phe, or an analogue thereof;

C is Trp, D-Pal, D-Nal, L-Nal-D-Pal(N—O), or D-Trp, or an analogue thereof;

D is Ser, or an analogue thereof;

E is N-Me-Ala, Tyr, N-Me-Tyr, Ser, Lys(iPr), 4-Cl-Phe, His, Asn, Met, Ala, Arg or Ile, or an analogue thereof;

F is D-Asn;

G is Leu or Trp, or an analogue thereof;

H is Lys(iPr), Gln, Met, or Arg, or an analogue thereof; and

I is Pro, or an analogue thereof;

or a pharmaceutically acceptable salt thereof.

13. A method of treating a subject having a disorder associated with LHRH activity, comprising administering to a subject an effective amount of a peptide compound which inhibits LHRH activity, wherein the peptide compound comprises a structure:

B-C-D-E-F-G-H-I-J wherein

B is D-His, L-His, or an analogue thereof;

C is D-Trp, L-Trp, or an analogue thereof;

D is D-Ser, L-Ser, or an analogue thereof;

E is D-Tyr, L-Tyr, or an analogue thereof;

F is D-asparagine, L-asparagine, D-glutamine, or L-glutamine;

G is D-Leu, L-Leu or an analogue thereof;

H is D-Arg, L-Arg, or an analogue thereof;

I is D-Pro, L-Pro, or an analogue thereof; and

J is D-Gly, L-Gly, or an analogue thereof;

or a pharmaceutically acceptable salt thereof.

14. The method of any one of claim 1, 2, 5, 6, 7, 8, 9, 10, 11, 12, or 13, wherein said disorder associated with LHRH activity is selected from the group consisting of precocious puberty, prostate cancer, ovarian cancer, benign prostatic hypertrophy, endometriosis, uterine fibroids, breast cancer, premenstrual syndrome, and polycystic ovary syndrome.

15. The method of any one of claim 1, 3, 5, 6, 7, 8, 9, 10, 11, 12, or 13, wherein said disorder associated with LHRH activity is precocious puberty.

16. The method of any one of claim 1, 2, 5, 6, 7, 8, 9, 10, 11, 12, or 13, wherein said disorder associated with LHRH activity is prostate cancer.

17. The method of any one of claim 1, 2, 5, 6, 7, 8, 9, 10, 11, 12, or 13, wherein said disorder associated with LHRH activity is ovarian cancer.

18. The method of The method of any one of claim 1, 2, 5, 6, 7, 8, 9, 10, 11, 12, or 13, wherein said disorder associated with LHRH activity is benign prostatic hypertrophy.

19. The method of any one of claim 1, 2, 5, 6, 7, 8, 9, 10, 11, 12, or 13, wherein said disorder associated with LHRH activity is endometriosis.

20. The method of any one of claim 1, 2, 5, 6, 7, 8, 9, 10, 11, 12, or 13, wherein said disorder associated with LHRH activity is uterine fibroids.

21. The method of any one of claim 1, 2, 5, 6, 7, 8, 9, 10, 11, 12, or 13, wherein said disorder associated with LHRH activity is breast cancer.

22. The method of any one of claim 1, 2, 5, 6, 7, 8, 9, 10, 11, 12, or 13, wherein said disorder associated with LHRH activity is premenstrual syndrome.

23. The method of any one of claim 1, 2, 5, 6, 7, 8, 9, 10, 11, 12, or 13, wherein said disorder associated with LHRH activity is polycystic ovary syndrome.

* * * * *

UNITED STATES PATENT AND TRADEMARK OFFICE
CERTIFICATE OF CORRECTION

PATENT NO. : 6,455,499 B1
DATED : September 24, 2002
INVENTOR(S) : Roger W. Roeske It is certified that error appears in the above-identified patent and that said Letters Patent is hereby corrected as shown below:

<u>Column 1,</u>
Line 3, please insert the following government support clause:
-- Government Support
 This invention was made with government support under Grant Number HD33172 awarded by the National Institutes of Health. The government has certain rights in the invention. --

Signed and Sealed this

Tenth Day of February, 2004

JON W. DUDAS
*Acting Director of the United States Patent and Trademark Office*

SEQUENCE LISTING

```
<160> NUMBER OF SEQ ID NOS: 1

<210> SEQ ID NO 1
<211> LENGTH: 10
<212> TYPE: PRT
<213> ORGANISM: Homo sapiens

<400> SEQUENCE: 1

Glu His Trp Ser Tyr Gly Leu Arg Pro Gly
 1               5                  10
```